United States Patent
Sun et al.

(10) Patent No.: US 10,941,199 B2
(45) Date of Patent: *Mar. 9, 2021

(54) ANTI-CD79B ANTIBODIES AND METHODS OF USE

(71) Applicant: Genentech, Inc., South San Francisco, CA (US)

(72) Inventors: Liping L. Sun, San Ramon, CA (US); Yvonne Man-Yee Chen, Hillsborough, CA (US); Mark S. Dennis, San Carlos, CA (US); Allen J. Ebens, Jr., San Carlos, CA (US); Andrew Polson, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/957,157

(22) Filed: Apr. 19, 2018

(65) Prior Publication Data

US 2018/0327492 A1 Nov. 15, 2018

Related U.S. Application Data

(63) Continuation of application No. 14/960,015, filed on Dec. 4, 2015, now Pat. No. 9,975,949.

(60) Provisional application No. 62/088,487, filed on Dec. 5, 2014.

(51) Int. Cl.
*A61K 39/00* (2006.01)
*C07K 16/28* (2006.01)
*A61K 47/68* (2017.01)

(52) U.S. Cl.
CPC ...... *C07K 16/2803* (2013.01); *A61K 47/6803* (2017.08); *A61K 47/6849* (2017.08); *C07K 16/2809* (2013.01); *A61K 2039/505* (2013.01); *C07K 2317/21* (2013.01); *C07K 2317/24* (2013.01); *C07K 2317/31* (2013.01); *C07K 2317/34* (2013.01); *C07K 2317/55* (2013.01); *C07K 2317/622* (2013.01); *C07K 2317/92* (2013.01)

(58) Field of Classification Search
CPC ............ C07K 16/2803; C07K 16/2809; A61K 47/6803; A61K 47/6849; A61P 35/00
See application file for complete search history.

(56) References Cited

U.S. PATENT DOCUMENTS

| | | | |
|---|---|---|---|
| 5,821,337 | A | 10/1998 | Carter et al. |
| 8,088,378 | B2 | 1/2012 | Chen et al. |
| 8,545,850 | B2 | 10/2013 | Chen et al. |
| 8,652,479 | B2 | 2/2014 | Ebens, Jr. et al. |
| 8,709,421 | B2 | 4/2014 | Heiss |
| 9,085,630 | B2 | 7/2015 | Crowley et al. |
| 9,308,257 | B2 | 4/2016 | Sharma et al. |
| 9,315,567 | B2 | 4/2016 | Chang et al. |
| 9,657,102 | B2 | 5/2017 | Smith et al. |
| 9,975,949 | B2* | 5/2018 | Sun ..................... A61K 47/6803 |
| 2010/0150918 | A1 | 6/2010 | Kufer et al. |
| 2011/0070243 | A1 | 3/2011 | Crowley et al. |
| 2013/0078249 | A1 | 3/2013 | Ast et al. |
| 2013/0287774 | A1 | 10/2013 | Zugmaier et al. |
| 2014/0242079 | A1 | 8/2014 | Bacac et al. |
| 2014/0302064 | A1 | 10/2014 | Moore et al. |
| 2014/0377270 | A1 | 12/2014 | Moore et al. |
| 2015/0166661 | A1* | 6/2015 | Chen .................... C07K 16/283 424/135.1 |
| 2016/0017058 | A1 | 1/2016 | Kim et al. |
| 2016/0075785 | A1 | 3/2016 | Ast et al. |
| 2016/0090416 | A1 | 3/2016 | Gunde et al. |
| 2016/0368985 | A1 | 12/2016 | Hotzel et al. |
| 2016/0368994 | A1 | 12/2016 | Kelley et al. |
| 2017/0008971 | A1 | 1/2017 | Dennis et al. |

FOREIGN PATENT DOCUMENTS

| | | |
|---|---|---|
| CL | 200802083 | 11/2008 |
| CL | 200900062 | 5/2010 |
| CL | 201500028 | 2/2015 |
| CN | 101802012 A | 8/2010 |
| EP | 2066349 B1 | 3/2012 |
| JP | 2008-501621 A | 1/2008 |
| JP | 2010-533495 A | 10/2010 |
| JP | 2011-514146 A | 5/2011 |
| JP | 2011-515069 A | 5/2011 |
| WO | 2008/119566 | 10/2008 |
| WO | 2009/012256 A1 | 1/2009 |
| WO | 2009/012268 A1 | 1/2009 |
| WO | 2009/099179 | 8/2009 |
| WO | 2009/099719 A2 | 8/2009 |
| WO | 2009/099728 | 8/2009 |
| WO | 2011/143545 A1 | 11/2011 |
| WO | 2012018687 | 2/2012 |
| WO | 2012/162067 A1 | 11/2012 |
| WO | 2012/162067 A2 | 11/2012 |
| WO | 2014/011521 | 1/2014 |

(Continued)

OTHER PUBLICATIONS

Strome et al., The Oncologist, 2007; 12:1084-95 (Year: 2007).*
Brand et al., Anticancer Res. 2006; 26:463-70 (Year: 2006).*
Alfarano et al. et al., "An alternatively spliced form of CD79b gene may account for altered B-cell receptor expression in B-chronic lymphocytic leukemia" Blood 93(7):2327-2335 (Apr. 1, 1999).
Cabezudo et al. et al., "Quantitative analysis of CD79b, CD5 and CD19 in mature B-cell lymphoproliferative disorders" Haematologica 84(5):413-418 (May 1999).
Carter, Paul, "Bispecific human IgG by design" J Immunol Methods 248(1-2):7-15 (Feb. 1, 2001).
Cragg, "The alternative transcript of CD79b is overexpresssed in B-CLL and inhibits signaling for apoptosis" Blood 100(9):3068-3076 (Nov. 1, 2002).

(Continued)

*Primary Examiner* — Sheela J. Huff
(74) *Attorney, Agent, or Firm* — Charles K. Sholtz

(57) ABSTRACT

The invention provides anti-CD79b antibodies and methods of using the same.

23 Claims, 9 Drawing Sheets

Specification includes a Sequence Listing.

(56) References Cited

FOREIGN PATENT DOCUMENTS

| WO | 2014/131712 A1 | 9/2014 |
|---|---|---|
| WO | 2014/151910 A1 | 9/2014 |

OTHER PUBLICATIONS

Dornan et al., "Therapeutic potential of an anti-CD79b antibody-drug conjugate, anti-CD79b-vc-MMAE, for the treatment of non-Hodgkin lymphoma" Blood 114(13):2721-9 ( 2009).

Haggart et al., "Cloning of a hamster anti-mouse CD79B antibody sequences and identification of a new hamster immunoglobulin lambda constant IGLC gene region" Immunogenetics 26:473-478 ( 2013).

Hashimoto et al. et al., "Alternative splicing of CD79a (Ig-alpha/mb-1) and CD79b (Ig-beta/B29) RNA transcripts in human B cells" Mol Immunol 32(9):651-659 (Jun. 1995).

Holliger, P., et al., "Specific killing of lymphoma cells by cytotoxic T-cells mediated by a bispecifc diabody" Protein Eng 9(3):299-305 (Mar. 1, 1996).

Honeychurch et al., "Bispecific Ab therapy of B-cell lymphoma: target cell specificity of antibody derivatives appears critical in determining therapeutic outcome" Cancer Immunol Immunother 45:171-173 ( 1997).

Kontermann, "Dual targeting strategies with bispecific antibodies" mAbs (Mar./Apr. 2012), 4(2):182-197.

Lu D. et al., "Pharmacokinetics (PK) of Anti-CD22 and Anti-CD79B Antibody Drug Conjugates (ADCS) in Relapsed or Refractory B-Cell Non-Hodgkin's Lymphoma (NHL Patients: Results from Phase I Dose-Escalation Studies" Clinical Pharmacology & Therapeutics 93( Suppl 1):S77-S78 (Feb. 2013).

Merchant et al., "An efficient route to human bispecific IgG" Nat Biotechnol 16(7):677-681 ( 1998).

Moore et al., "Application of dual affinity retargeting molecules to achieve optimal redirected T-cell killing of B-cell lymphoma" Blood 117(17):4542-51 ( 2011).

Morschhauser et al., "Updated Results of a Phase II Randomized Study (ROMULUS) of Polutuzumab Vedotin or Pinatuzumab Vedotin Plus Rituximab in Patients with Relapsed/Refractory Non-Hodgkin Lymphoma" Blood 124:4457 ( 2014).

Nagorsen et al., "Immunomodulatory therapy of cancer with T-cell-engaging BiTE antibody" Exp Cell Res. 317(9):1255-60 ( 2011).

Okazaki et al. et al., "Three new monoclonal antibodies that define a unique antigen associated with prolymphocytic leukemia/non-Hodgkin's lymphoma and are effectively internalized after binding to the cell surface antigen" Blood 81(1):84-94 (Jan. 1, 1993).

Palanca-Wessels et al., "A Phase I Study of the Anti-CD79b Antibody-Drug Conjugate (ADC) DCDS4501A Targeting CD79b in Relapsed or Refractory B-Cell Non-Hodgkin's Lymphoma (NHL)" Blood 120(21):56 (Nov. 21, 2012).

Pessano et al., "The T3/T cell receptor complex: antigenic distinction between the two 20-kd T3 subunits" EMBO Journal 4(2):337-344 ( 1985).

Polson et al., "Antibody-drug conjugates targeted to CD79 for the treatment of non-Hodgkin lymphoma" Blood 110:616-623 (Jul. 15, 2007).

Ridgway, J., et al., "Knobs-into-holes' engineering of antibody CH3 domains for heavy chain heterodimerization" Protein Eng 9(7):617-621 (Jul. 1, 1996).

Riedle et al., "In Vivo Activation and Expansion of T Cells by a Bi-Specific Antibody Abolishes Metastasis Formation of Human Melanoma Cells" Int. J. Cancer 75:908-918 ( 1998).

Written Opinion for PCT.US2015/063902 ( dated Feb. 17, 2016).

Zheng et al., "In vivo effects of targeting CD79 with antibodies and antibody-drug conjugates" Mol Cancer Ther 8(10) (Oct. 6, 2009).

Zhu et al., "Expression of CD22 and CD79b from patients with chronic lymphocytic leukemia" Journal of Clinical Hema (published in Chinese, with English translation of the abstract provided), 26(10):667-669 ( 2013).

Zhu, Z. et al. et al., "Engineering High Affinity Humanized Anti-p185HER2/Anti-CD3 Bispecific F(ab')2 for Efficient Lysis of p185HER2 Overexpressing Tumor Cells" Int J Cancer 62:319-324 ( 1995).

Zomas et al., "Expression of the immunoglobulin-associated protein B29 in B cell disorders with the monoclonal antibody SN8 (CD79b)" Leukemia 10:1966-1970 ( 1996).

Brown et al., "Tolerance of single, but not multiple, amino acid replacements in antibody VH CDR 2: a means of minimizing B cell wastage from somatic hypermutation?" The Journal of Immunology 156(9):3285-3291 (1996).

Casset et al., "A peptide mimetic of an anti-CD4 monoclonal antibody by rational design" Biochem Bioph Res Co 307(1):198-205 (Jul 18, 2003).

De Pascalis et al., J Immunol 169(6):3076-3084 (2002).

Paul, William E., "Fundamental Immunology" Raven Press( SUPPL Chpt. 8):292-295.

Rudikoff et al., "Single amino acid substitution altering antigen-binding specificity" P Natl Acad Sci USA 79:1979-1983 (Mar 1982).

Vajdos et al., "Comprehensive Antibody Obtained with Shotgun Functional Maps of the AntigenScanning Mutagenesis" J. -binding Site of an Anti-ErbB2 Mol. Biol. 320:415-428 (2002).

* cited by examiner

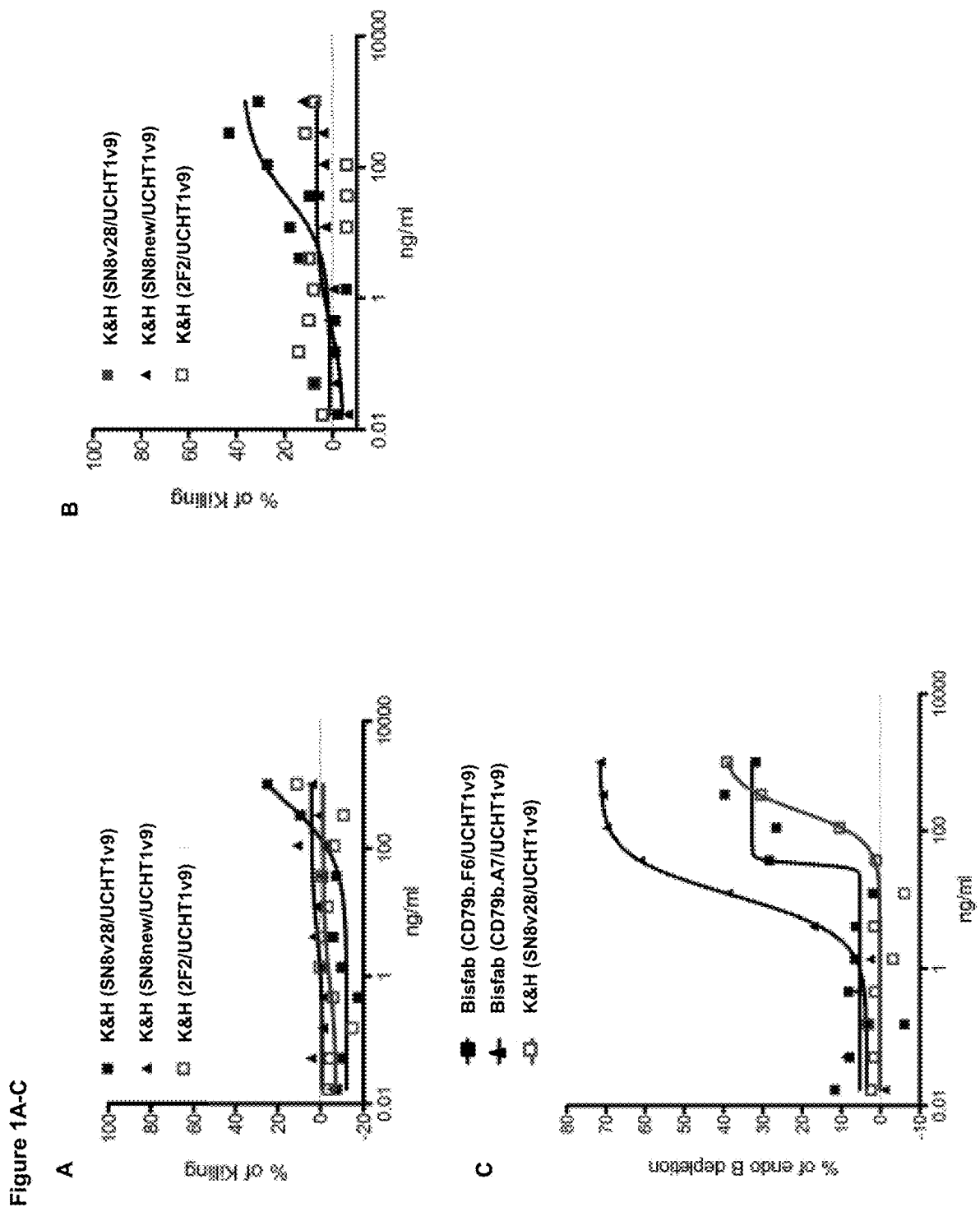
Figure 1A-C

Figure 2A-D
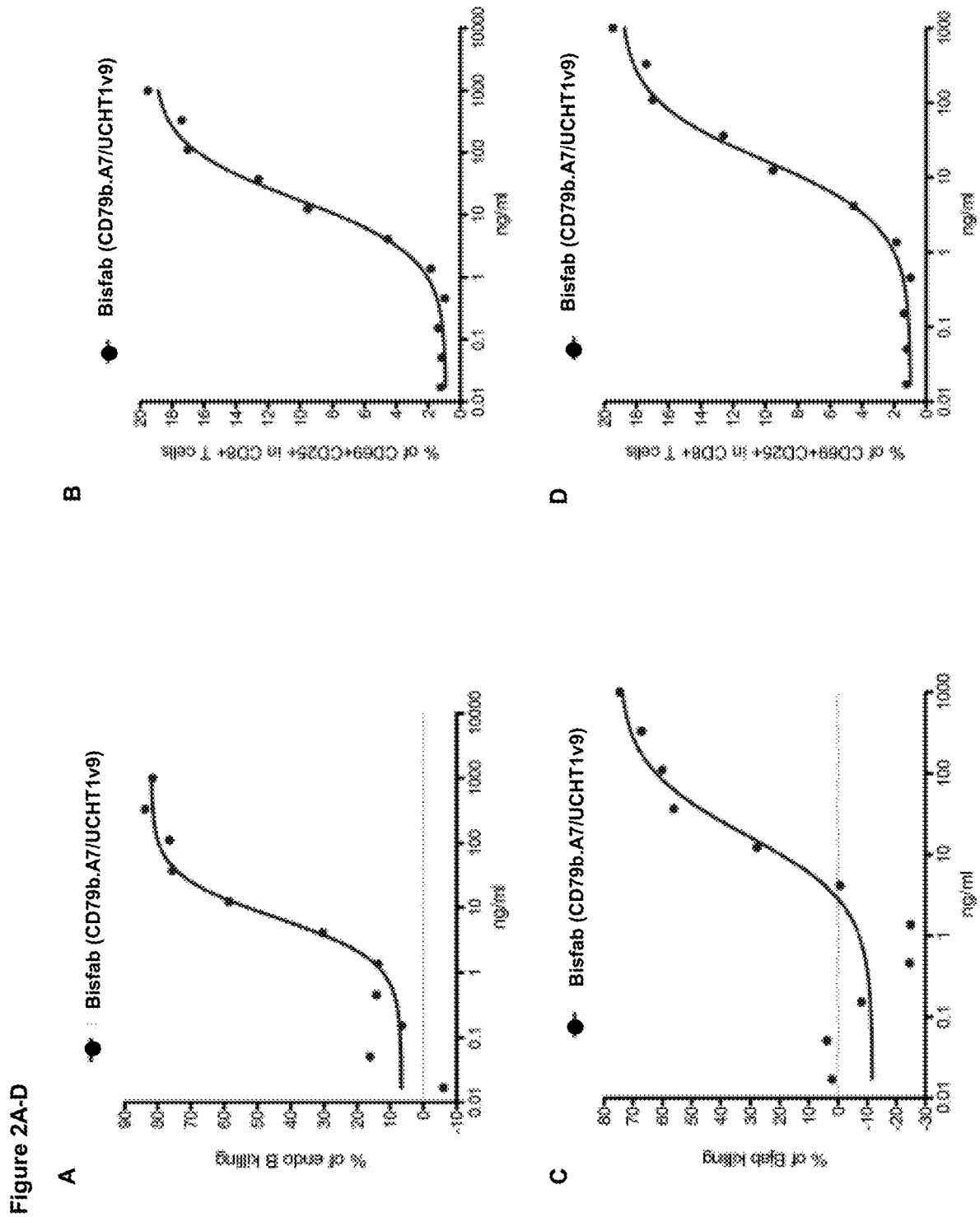

Figure 3A-C
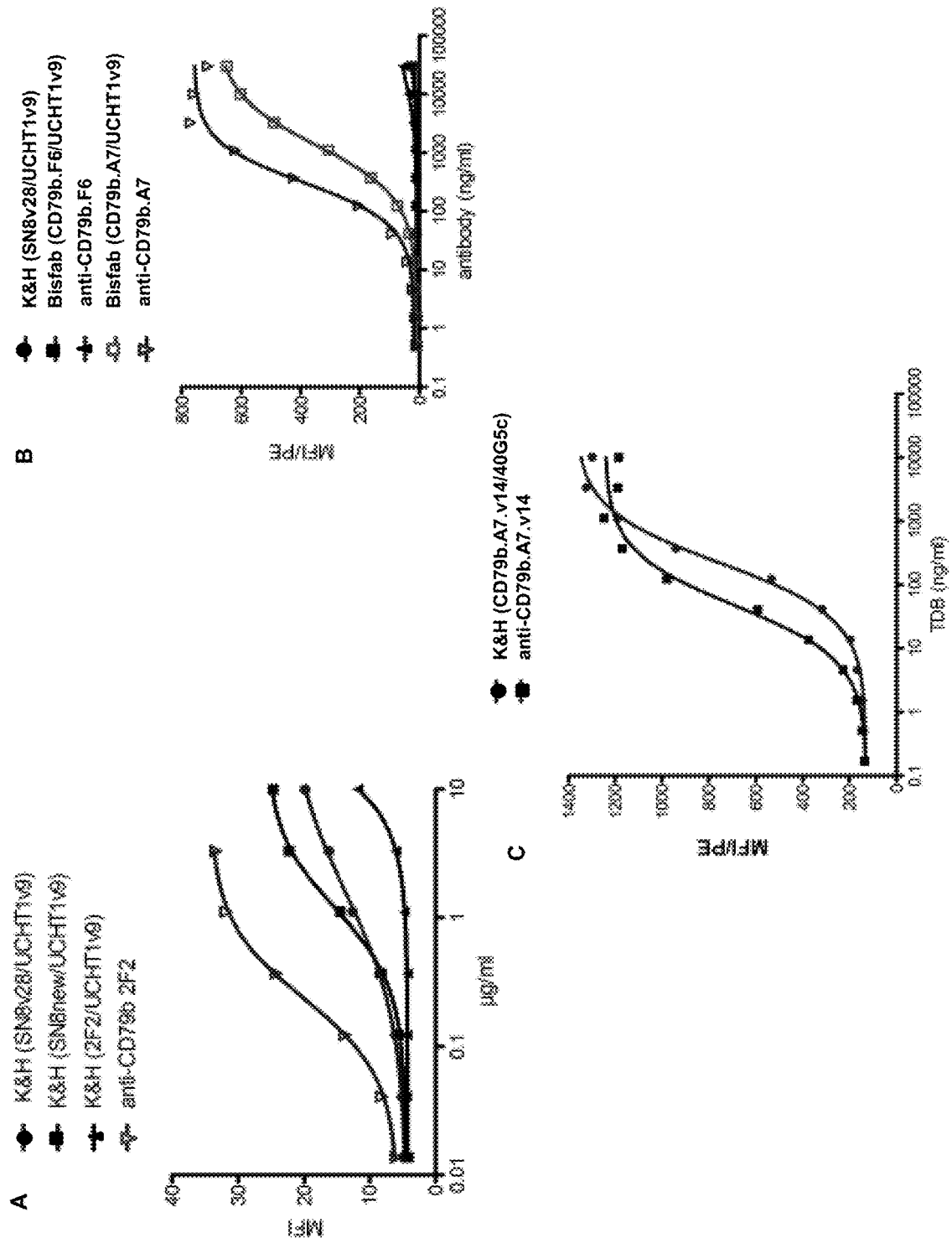

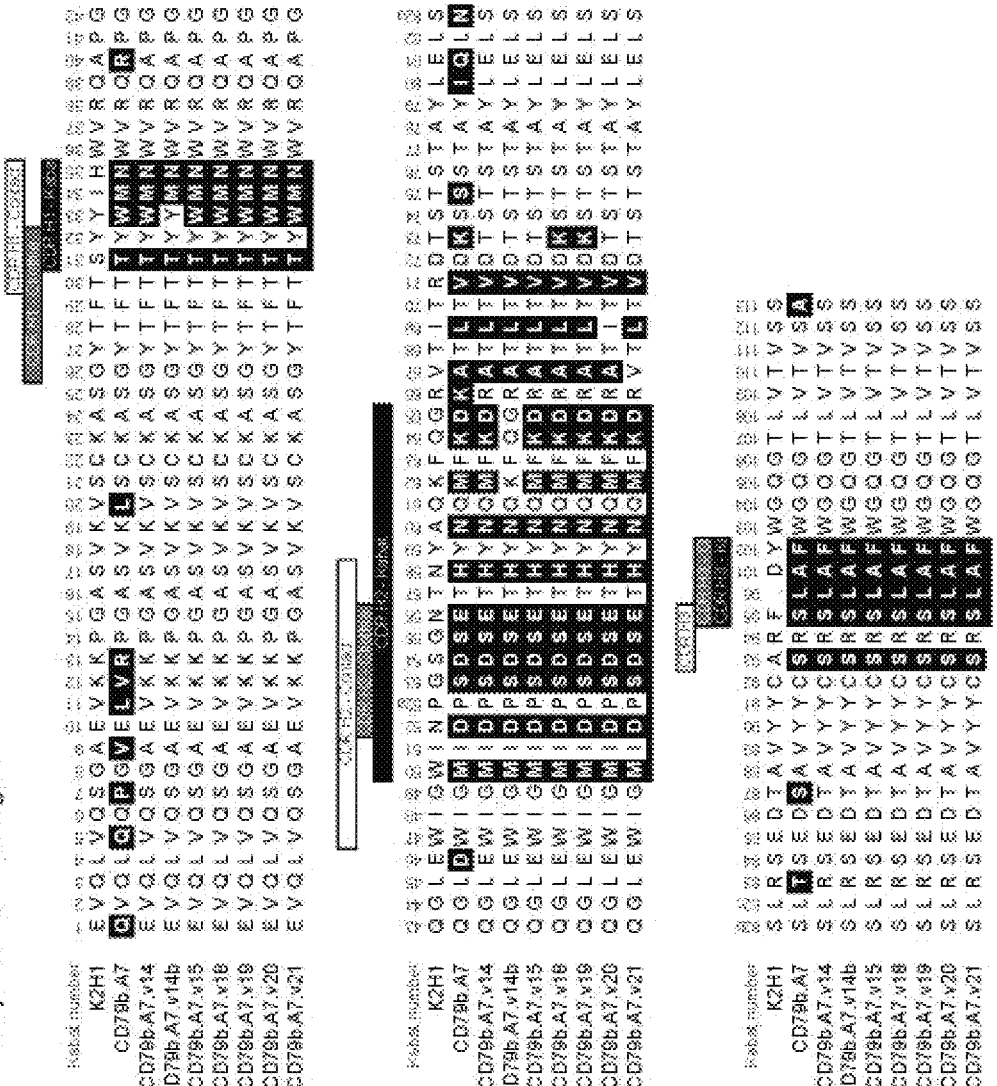
Figure 4A-B

Figure 4A-B

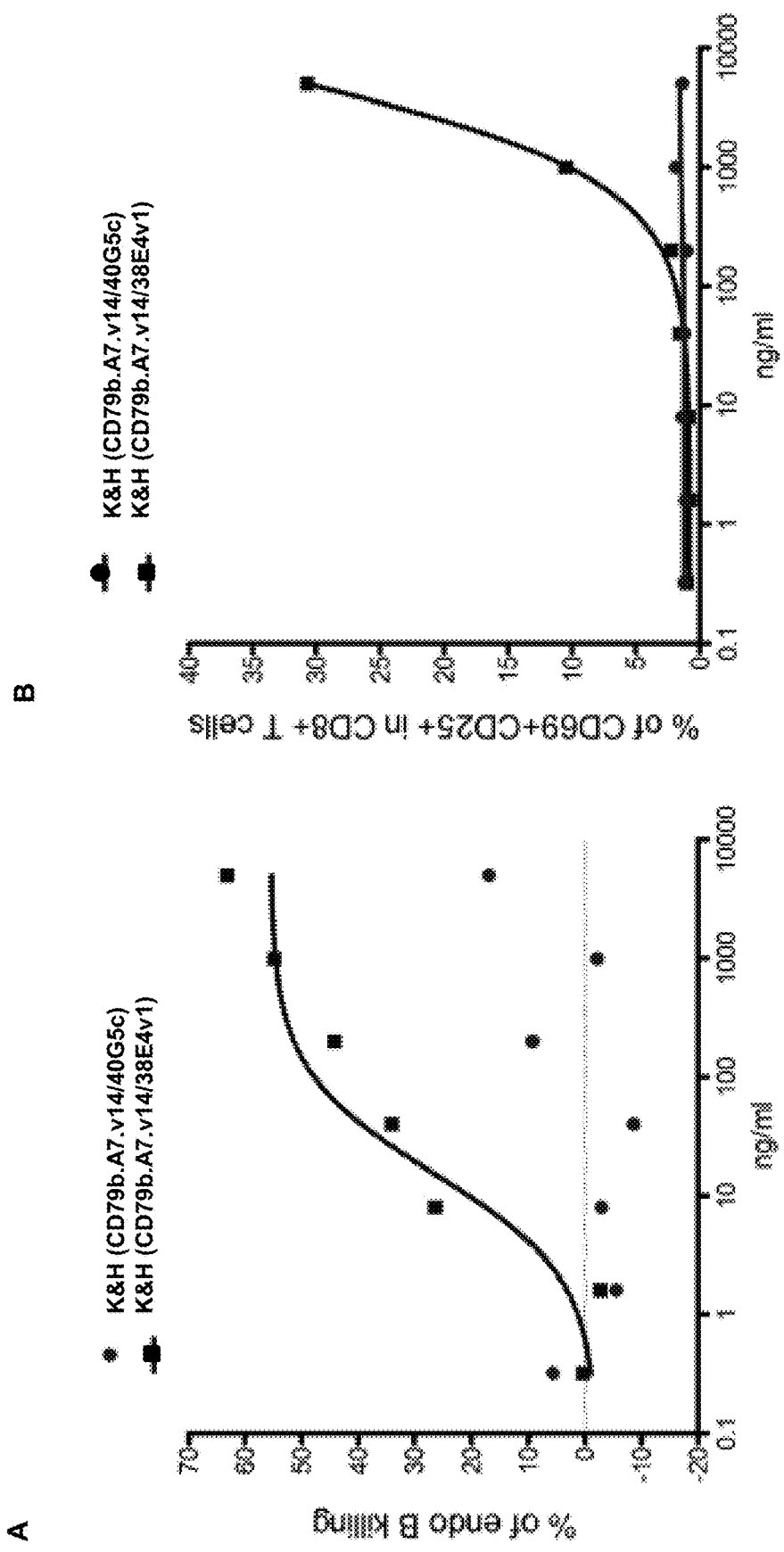
Figure 5A-B

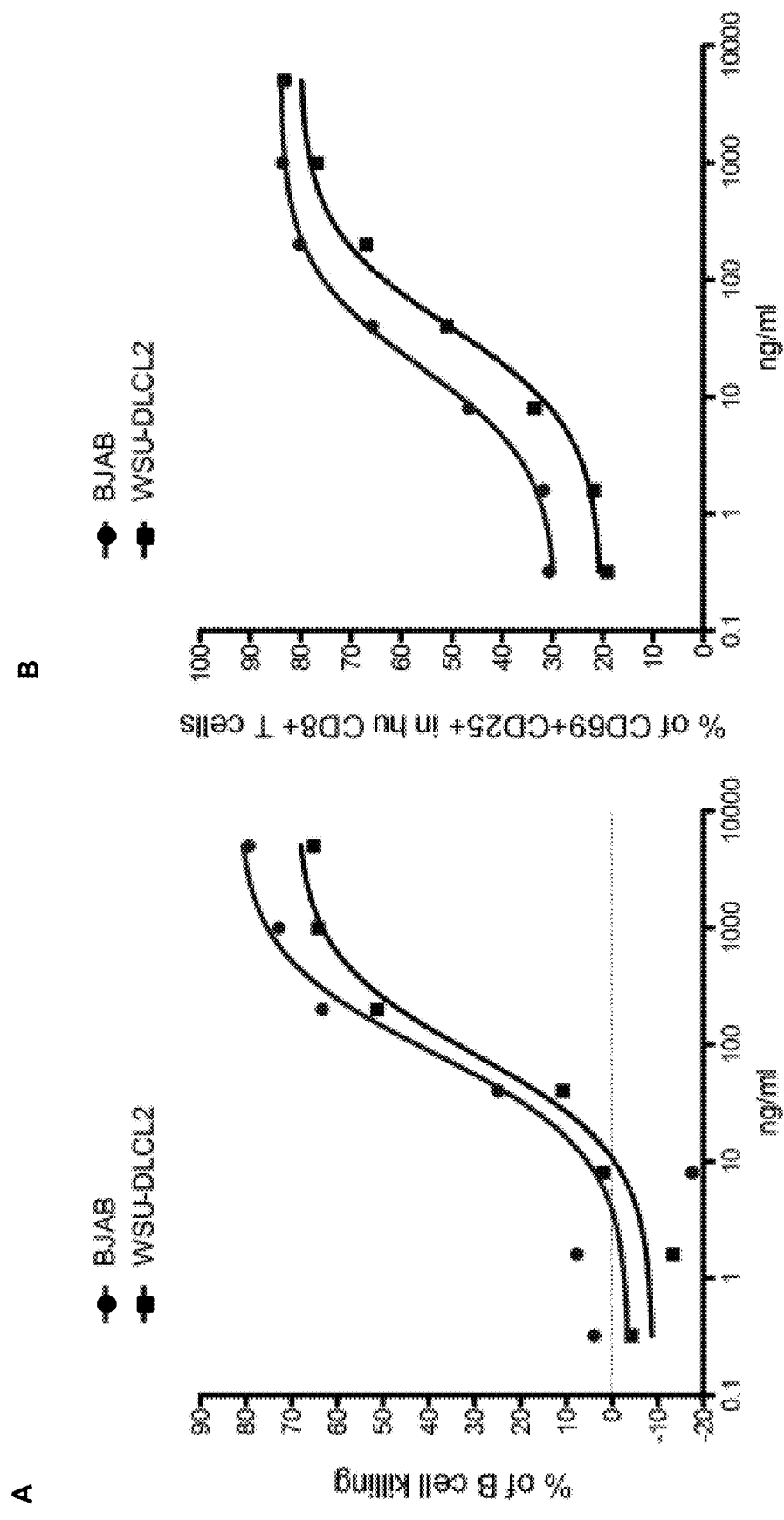
Figure 6A-B

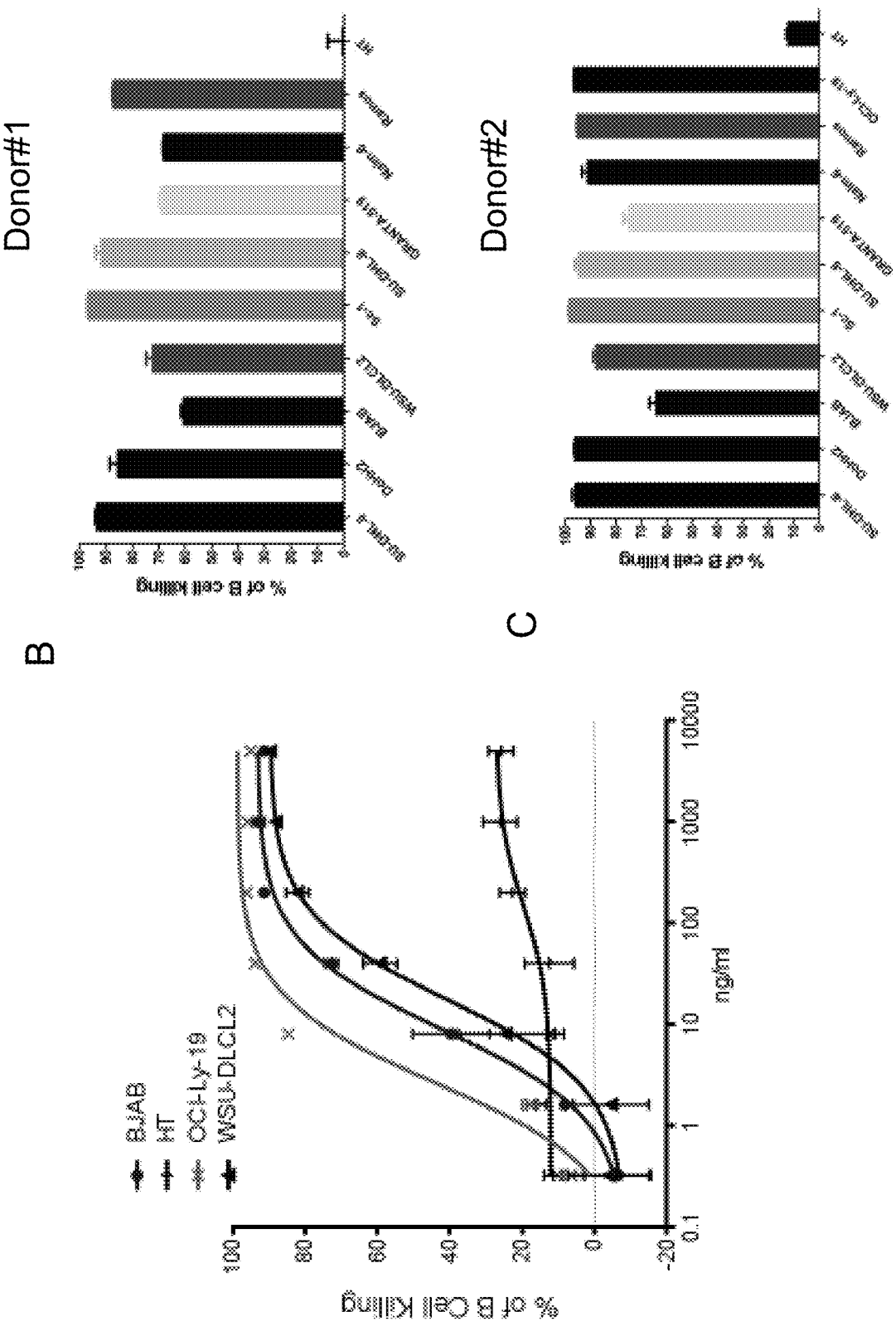
Figure 7A-C

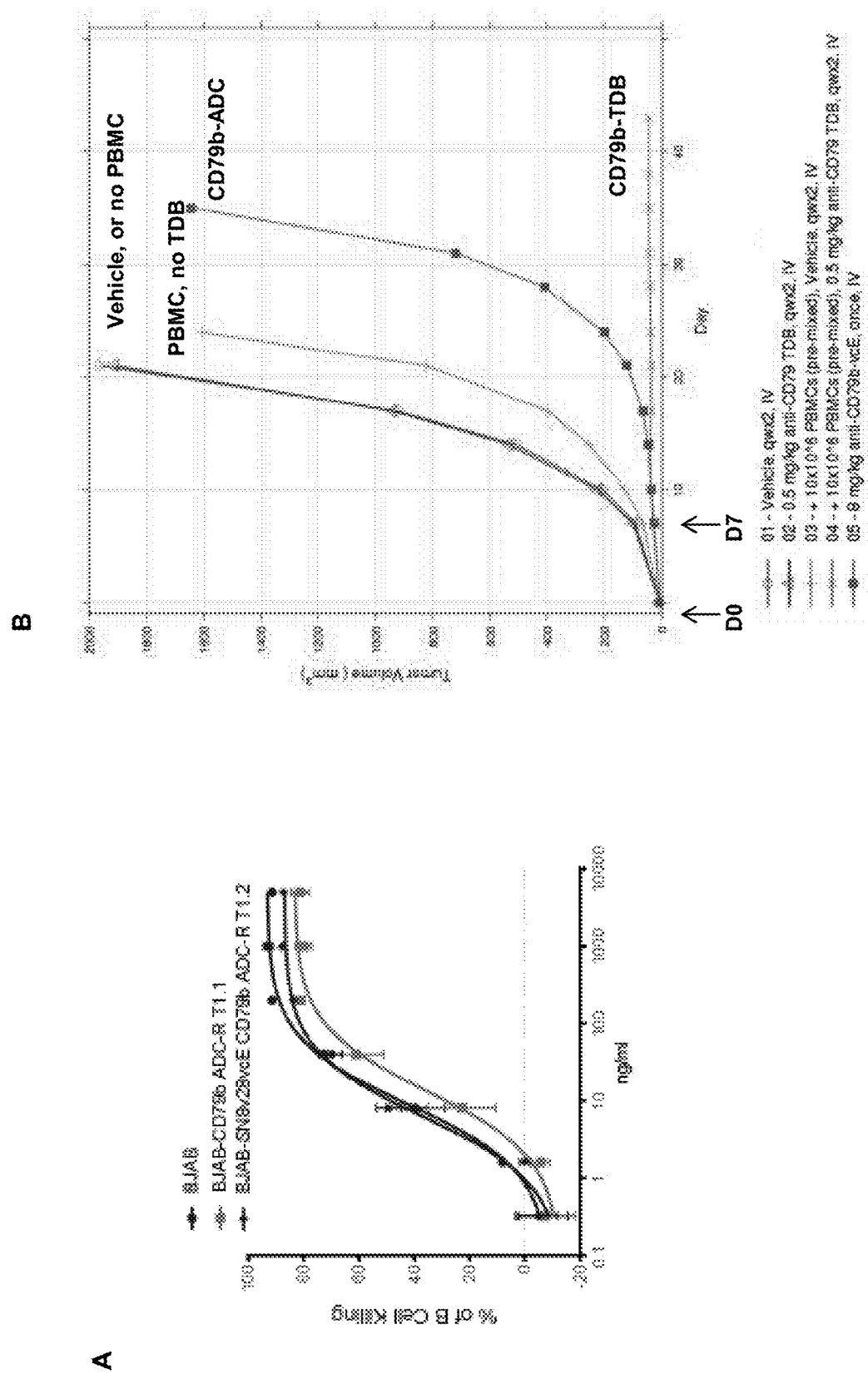
Figure 8A-B

ANTI-CD79B ANTIBODIES AND METHODS OF USE

CROSS REFERENCE TO RELATED APPLICATION

This application is a continuation of U.S. patent application Ser. No. 14/960,015 filed on Dec. 4, 2015 which claims the benefit of priority to U.S. Provisional Application No. 62/088,487 filed Dec. 5, 2014, which is herein incorporated by reference in its entirety.

SEQUENCE LISTING

The instant application contains a Sequence Listing which has been submitted electronically in ASCII format and is hereby incorporated by reference in its entirety. Said ASCII copy, created on Apr. 19, 2018, is named P32464-US-2_SL.txt and is 41,735 bytes in size.

FIELD OF THE INVENTION

The present invention relates to anti-CD79b antibodies including anti-CD79b antibodies comprising a CD3 binding domain (e.g., anti-CD79b/CD3 T cell dependent bispecific (TDB) antibody) and methods of using the same.

BACKGROUND

Cell proliferative disorders, such as cancer, are characterized by the uncontrolled growth of cell subpopulations. They are the leading cause of death in the developed world and the second leading cause of death in developing countries, with over 12 million new cancer cases diagnosed and 7 million cancer deaths occurring each year. The National Cancer Institute estimates that greater than half a million Americans will die of cancer in 2013, accounting for nearly one out of every four deaths in the country. As the elderly population has grown, the incidence of cancer has concurrently risen, as the probability of developing cancer is more than two-fold higher after the age of seventy. Cancer care thus represents a significant and ever-increasing societal burden.

CD79b is the signaling component of the B-cell receptor and acts as a covalent heterodimer containing CD79a (i.e., Igα or mb-1) and CD79b (i.e., Igβ or B29). CD79b contains an extracellular immunoglobulin (Ig) domain, a transmembrane domain, and an intracellular signaling domain, an immunoreceptor tyrosine-based activation motif (ITAM) domain. By using flow cytometry, surface expression of CD79b has been detected in almost all non-Hodgkin lymphoma (NHL) and chronic lymphocytic leukemia (CLL) patients. Dornan et al., Blood 114(13):2721-9 (2009). In addition to its signaling functions, when the B-cell receptor is cross-linked, it is targeted to the major histocompatibility complex class II compartment, a lysosome-like compartment, as part of class II antigen presentation by B cells.

This feature of CD79b biology makes it a particularly attractive target for the use of ADCs because antibodies against CD79b are internalized and delivered to these lysosomal compartments, which are known to contain protease that can release the cytotoxic drug. Therefore, antibody-drug conjugates (ADC) have been generated (such as the humanized anti-CD79b antibody (humanized SN8) conjugated to monomethyllauristatin E (MMAE) by a protease cleavable linker), which has shown to be clinical efficacious for the treatment of NHL. See e.g., U.S. Pat. No. 8,088,378 and Morschhauser et al., "4457 Updated Results of a Phase II Randomized Study (ROMULUS) of Polatuzumab Vedotin or Pinatuzumab Vedotin Plus Rituximab in Patients with Relapsed/Refractory Non-Hodgkin Lymphoma" 56th ASH Annual Meeting and Exposition: Dec. 6-9, 2014. Despite the advances in NHL and CLL treatment using anti-CD79b ADC therapeutics, there still remains an unmet need for improved therapies for NHL and CLL patients, in particular those resistant to anti-CD79b ADC therapies.

Recently, bispecific antibody-based immunotherapies have been developed, which are capable of simultaneously binding cell surface antigens on cytotoxic cells and tumor cells with the intent that the bound cytotoxic cell will destroy the bound tumor cell. Such bispecific antibodies may have advantages, e.g., efficacy and/or safety compared to the antibody-drug conjugate. Thus, there is an unmet need in the field for the development of effective bispecific antibodies for use in cancer treatment.

SUMMARY

The invention provides anti-CD79b antibodies and methods of using the same. In particular provided herein are anti-CD79b antibodies comprising a CD79b binding domain and a CD3 binding domain.

In one aspect, provided herein are isolated anti-CD79b antibodies, the antibody comprises a CD79b binding domain comprising the following six hypervariable regions (HVRs): (a) an HVR-H1 comprising the amino acid sequence of SEQ ID NO: 5; (b) an HVR-H2 comprising the amino acid sequence of SEQ ID NO: 8; (c) an HVR-H3 comprising the amino acid sequence of SEQ ID NO: 9; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 12.

In some embodiments, the CD79b binding domain comprises the following six HVRs: (a) an HVR-H1 comprising the amino acid sequence of SEQ ID NO: 3; (b) an HVR-H2 comprising the amino acid sequence of SEQ ID NO: 6; (c) an HVR-H3 comprising the amino acid sequence of SEQ ID NO: 9; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 12. In some embodiments, the anti-CD79b antibody comprises (a) a VH sequence having at least 95% sequence identity to the amino acid sequence of SEQ ID NO:17, 21, 23, 25, 27 or 29; (b) a VL sequence having at least 95% sequence identity to the amino acid sequence of SEQ ID NO:18, 22, 24, 26, 28, or 30; or (c) a VH sequence as in (a) and a VL sequence as in (b). In some embodiments, the anti-CD79b comprises a VH sequence of SEQ ID NO: 17, 21, 23, 25, 27 or 29. In some embodiments, the anti-CD79b antibody comprises a VL sequence of SEQ ID NO: 18, 22, 24, 26, 28, or 30.

In some embodiments, the CD79b binding domain comprises the following six HVRs: (a) an HVR-H1 comprising the amino acid sequence of SEQ ID NO: 4; (b) an HVR-H2 comprising the amino acid sequence of SEQ ID NO: 7; (c) an HVR-H3 comprising the amino acid sequence of SEQ ID NO: 9; (d) an HVR-L1 comprising the amino acid sequence of SEQ ID NO: 10; (e) an HVR-L2 comprising the amino acid sequence of SEQ ID NO: 11; and (f) an HVR-L3 comprising the amino acid sequence of SEQ ID NO: 12. In some embodiments, the anti-CD79b antibody comprises (a) a VH sequence having at least 95% sequence identity to the amino acid sequence of SEQ ID NO:19; (b) a VL sequence having at least 95% sequence identity to the amino acid sequence of SEQ ID NO:20; or (c) a VH sequence as in (a) and a VL sequence as in (b). In some embodiments, the anti-CD79b antibody comprises a VH sequence of SEQ ID NO:19. In some embodiments, the anti-CD79b antibody comprises a VL sequence of SEQ ID NO:20.

In some embodiments of any of the anti-CD79b antibodies, the CD79b binding domain binds to SEQ ID NO:63.

In some embodiments of any of the anti-CD79b antibodies, the anti-CD79b antibody (e.g., CD79b binding domain) binds human CD79b with a Kd of less than about 25 nM as a dual arm, bivalent IgG antibody, e.g., less than about any of 10 nM or 5 nM. In some embodiments, Kd is determined by BIACORE. In some embodiments, Kd is determined by CD79b immobilized at a low density. In some embodiments of any of the anti-CD79b antibodies, the anti-CD79b antibody (e.g., CD79b binding domain) binds a B cell (e.g., BJAB cell) at an $EC_{50}$ of less than about 150 ng/mL as a dual arm, bivalent IgG antibody, e.g., less than about any of 100 ng/mL, 75 ng/mL, or 50 ng/mL. In some embodiments, binding to a B cell is determined by FACS. In some embodiments of any of the anti-CD79b antibodies, the anti-CD79b antibody (e.g., CD79b binding domain) binds human CD79b binds a B cell (e.g., BJAB cell) at an $EC_{50}$ of less than about 1.5 ug/mL in a monovalent format (e.g., an anti-CD79b bispecific antibody comprising a CD79b and CD3 binding domain), e.g., less than about 1 ug/mL, 0.75 ug/mL, 0.5 ug/mL or 0.25 ug/mL. In some embodiments, binding to a B cell is determined by FACS.

In some embodiments of any of the anti-CD79b antibodies, the anti-CD79b antibody is a monoclonal, human, humanized, or chimeric antibody. In some embodiments of any of the anti-CD79b antibodies, the antibody is an IgG antibody. In some embodiments of any of the anti-CD79b antibodies, the antibody is an antibody fragment that binds CD79b. In some embodiments, the antibody fragment is a Fab, Fab'-SH, Fv, scFv, and/or (Fab')$_2$ fragment. In some embodiments of any of the anti-CD79b antibodies, the antibody is a full-length antibody.

In some embodiments of any of the anti-CD79b antibodies, the anti-CD79b antibody comprises an aglycosylation site mutation. In some embodiments, the aglycosylation site mutation is a substitution mutation.

In some embodiments of any of the anti-CD79b antibodies, the anti-CD79b antibody comprises reduced effector function. In some embodiments, the antibody comprises a substitution mutation is at amino acid residue N297, L234, L235, and/or D265 according to EU numbering. In some embodiments, the substitution mutation is selected from the group consisting of N297G, N297A, L234A, L235A, and D265A according to EU numbering. In some embodiments, the antibody comprises an N297G substitution mutation at amino acid residue 297 according to EU numbering.

In some embodiments of any of the anti-CD79b antibodies, the anti-CD79b antibody is a monospecific antibody (e.g., bivalent, dual arm antibody).

In some embodiments of any of the anti-CD79b antibodies, the anti-CD79b antibody is a multispecific antibody.

In some embodiments of any of the multispecific antibodies, the multispecific antibody comprises a CD3 binding domain. In some embodiments, the CD3 binding domain binds to a human CD3 polypeptide or a cynomolgus monkey (cyno) CD3 polypeptide. In some embodiments, the human CD3 polypeptide or the cyno CD3 polypeptide is a human CD3E polypeptide or a cyno CD3E polypeptide, respectively. In some embodiments, the human CD3 polypeptide or the cyno CD3 polypeptide is a human CD3γ polypeptide or a cyno CD3γ polypeptide, respectively.

In some embodiments of any of the multispecific antibodies, the CD3 binding domain binds the human CD3E polypeptide with a Kd of 250 nM or lower. In some embodiments, the CD3 binding domain binds the human CD3E polypeptide with a Kd of 100 nM or lower. In some embodiments, the CD3 binding domain binds the human CD3E polypeptide with a Kd of 15 nM or lower. In some embodiments, the CD3 binding domain binds the human CD3E polypeptide with a Kd of 10 nM or lower. In some embodiments, the CD3 binding domain binds the human CD3E polypeptide with a Kd of 5 nM or lower.

In some embodiments of any of the multispecific anti-CD79b antibodies, the CD3 binding domain comprises the following six HVRs: (a) an HVR-H1 comprising the amino acid sequence of SEQ ID NO:45; (b) an HVR-H2 comprising the amino acid sequence of SEQ ID NO:46; (c) an HVR-H3 comprising the amino acid sequence of SEQ ID NO:47; (d) an HVR-L1 comprising the amino acid sequence of SEQ ID NO:48; (e) an HVR-L2 comprising the amino acid sequence of SEQ ID NO:49; and (f) an HVR-L3 comprising the amino acid sequence of SEQ ID NO:50. In some embodiments of any of the multispecific anti-CD79b antibodies, the CD3 binding domain comprises (a) a VH sequence having at least 95% sequence identity to the amino acid sequence of SEQ ID NO:59; (b) a VL sequence having at least 95% sequence identity to the amino acid sequence of SEQ ID NO:60; or (c) a VH sequence as in (a) and a VL sequence as in (b). In some embodiments, the CD3 binding domain comprises a VH sequence of SEQ ID NO:59. In some embodiments, the CD3 binding domain comprises a VL sequence of SEQ ID NO:60.

In some embodiments of any of the multispecific anti-CD79b antibodies, the CD3 binding domain comprises the following six HVRs: (a) an HVR-H1 comprising the amino acid sequence of SEQ ID NO:39; (b) an HVR-H2 comprising the amino acid sequence of SEQ ID NO:40; (c) an HVR-H3 comprising the amino acid sequence of SEQ ID NO:41; (d) an HVR-L1 comprising the amino acid sequence of SEQ ID NO:42; (e) an HVR-L2 comprising the amino acid sequence of SEQ ID NO:43; and (f) an HVR-L3 comprising the amino acid sequence of SEQ ID NO:44. In some embodiments of any of the multispecific anti-CD79b antibodies, the CD3 binding domain comprises (a) a VH sequence having at least 95% sequence identity to the amino acid sequence of SEQ ID NO:57; (b) a VL sequence having at least 95% sequence identity to the amino acid sequence of SEQ ID NO:58; or (c) a VH sequence as in (a) and a VL sequence as in (b). In some embodiments, the CD3 binding domain comprises a VH sequence of SEQ ID NO:57. In some embodiments, the CD3 binding domain comprises a VL sequence of SEQ ID NO:58.

In some embodiments of any of the multispecific anti-CD79b antibodies, the CD3 binding domain comprises the following six HVRs: (a) an HVR-H1 comprising the amino acid sequence of SEQ ID NO:51; (b) an HVR-H2 comprising the amino acid sequence of SEQ ID NO:52; (c) an HVR-H3 comprising the amino acid sequence of SEQ ID NO:53; (d) an HVR-L1 comprising the amino acid sequence of SEQ ID NO:54; (e) an HVR-L2 comprising the amino acid sequence of SEQ ID NO:55; and (f) an HVR-L3 comprising the amino acid sequence of SEQ ID NO:56. In some embodiments of any of the multispecific anti-CD79b antibodies, the CD3 binding domain comprises (a) a VH sequence having at least 95% sequence identity to the amino acid sequence of SEQ ID NO:61; (b) a VL sequence having at least 95% sequence identity to the amino acid sequence of SEQ ID NO:62; or (c) a VH sequence as in (a) and a VL sequence as in (b). In some embodiments, the CD3 binding domain comprises a VH sequence of SEQ ID NO:61. In some embodiments, the CD3 binding domain comprises a VL sequence of SEQ ID NO:62.

In some embodiments of any of the multispecific anti-CD79b antibodies, the anti-CD79b antibody has a B cell killing $EC_{50}$ of less than about 100 ng/mL, e.g., less than about any of 50, 25, 20, or 15 ng/mL. In some embodiments, the B cell killing is endogenous B cell killing. In some embodiments, the B cell killing is cell line B cell killing, e.g., BJAB cell line, WSU-CLCL2 cell line, OCI-Ly-19 cell line. In some embodiments of any of the multispecific anti-CD79b antibodies, the anti-CD79b antibody has a cytotoxic T cell activation $EC_{50}$ is less than about any of 50 ng/mL, e.g., less than about any of 25 ng/mL or 20 ng/mL. In some embodiments, cytotoxic T cell activation is measured by % of CD69+CD25+ T cells in CD8+ T cells.

In some embodiments of any of the multispecific anti-CD79b antibodies, the multispecific antibody is a bispecific antibody.

In some embodiments of any of the multispecific anti-CD79b antibodies, (a) the CD3 binding domain comprises a Fc domain, wherein the Fc domain comprises T366S, L368A, Y407V, and N297G substitution mutations according EU numbering and (b) the CD79b binding domain comprises a Fc domain, wherein the Fc domain comprises T366W and N297G substitution mutations according EU numbering. In some embodiments of any of the multispecific anti-CD79b antibodies, (a) the CD79b binding domain comprises a Fc domain, wherein the Fc domain comprises T366S, L368A, Y407V, and N297G substitution mutations according EU numbering and (b) the CD3 binding domain comprises a Fc domain, wherein the Fc domain comprises T366W and N297G substitution mutations according EU numbering.

In some embodiments of any of the multispecific anti-CD79b antibodies, the anti-CD79b antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some embodiments, at least one of the one or more heavy chain constant domains is paired with another heavy chain constant domain. In some embodiments, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some embodiments, the $CH3_1$ and $CH3_2$ domains meet at an interface between said protuberance and cavity. In some embodiments, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In some embodiments, the $CH2_1$ and $CH2_2$ domains meet at an interface between said protuberance and cavity.

Provided herein are also isolated nucleic acids encoding an anti-CD79b antibody described herein. Further provided herein are vectors comprising an isolated nucleic acid encoding an anti-CD79b antibody described herein. Provided herein are host cells comprising a vector comprising an isolated nucleic acid encoding an anti-CD79b antibody described herein. In some embodiments, the host cell is a eukaryotic host cell. In some embodiments, the host cell is a mammalian host cell (e.g., CHO). In some embodiments, the host cell is a prokaryotic host cell. In some embodiments, the prokaryotic host cell is an *E. coli* host cell. Provided herein are further methods of producing the anti-CD79b antibody described herein, wherein the method comprising culturing the host cell described herein in a culture medium.

Further provided herein are immunoconjugates comprising an anti-CD79b antibody of described herein and a cytotoxic agent.

Provided herein are pharmaceutical compositions comprising the anti-CD79b antibody described herein.

Provided herein are anti-CD79b antibodies as described herein for use as a medicament. Provided herein are anti-CD79b antibody described herein for use in treating or delaying progression of a B cell proliferative disorder or an autoimmune disorder in a subject in need thereof. Provided herein are anti-CD79b antibodies as described herein for use in enhancing immune function in a subject having a B cell proliferative disorder or an autoimmune disorder. In some embodiments, the B cell proliferative disorder is a cancer. In some embodiments, the B cell proliferative disorder is lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and/or mantle cell lymphoma. In some embodiments of any of the B cell proliferative disorders, the B cell proliferative disorder is resistant to treatment with an anti-CD79b antibody drug conjugate (e.g., anti-CD79b MMAE antibody drug conjugate). In some embodiments, the autoimmune disorder is selected from the group consisting of rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome, glomerulonephritis, Neuromyelitis Optica (NMO) and IgG neuropathy.

Provided herein are uses of any of the anti-CD79b antibody described herein in the manufacture of a medicament for treating or delaying progression of a cell proliferative disorder or an autoimmune disorder. Provided herein are uses of any of the anti-CD79b antibody described herein in the manufacture of a medicament for enhancing immune function in a subject having a cell proliferative disorder or an autoimmune disorder. In some embodiments, the B cell proliferative disorder is a cancer. In some embodiments, the B cell proliferative disorder is lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and/or mantle cell lymphoma. In some embodiments of any of the B cell proliferative disorders, the B cell proliferative disorder is resistant to treatment with an anti-CD79b antibody drug conjugate (e.g., anti-CD79b MMAE antibody drug conjugate). In some embodiments, the autoimmune disorder is selected from the group consisting of rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome, glomerulonephritis, Neuromyelitis Optica (NMO) and IgG neuropathy.

Provided herein are methods of treating or delaying the progression of a cell proliferative disorder or an autoimmune disorder in a subject in need thereof, the method comprising administering to the subject an anti-CD79b antibody described herein. Provided herein are methods of enhancing immune function in a subject having a cell proliferative disorder or an autoimmune disorder, the method comprising administering to the subject an effective amount of an anti-CD79b antibody described herein. In some embodiments, the B cell proliferative disorder is a cancer. In some embodiments, the B cell proliferative disorder is lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and/or mantle cell lymphoma. In some embodiments of any of the B cell proliferative disorders, the B cell proliferative disorder is resistant to treatment with an anti-CD79b antibody drug conjugate (e.g., anti-CD79b MMAE antibody drug conjugate). In some embodiments, the autoimmune disorder is selected from the group consisting of rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome, glomerulonephritis, Neuromyelitis Optica (NMO) and IgG neuropathy.

In some embodiments of any of the methods, the anti-CD79b antibody binds to (a) a CD3 molecule located on an immune effector cell and (b) a CD79b molecule located on a B cell. In some embodiments, the anti-CD79b antibody activates the immune effector cell following binding to (a) and (b). In some embodiments of any of the methods, the activated immune effector cell is capable of exerting a cytotoxic effect and/or an apoptotic effect on the target cell.

In some embodiments of any of the methods, the method further comprises administering to the subject a PD-1 axis binding antagonist or an additional therapeutic agent. In some embodiments, the PD-1 axis binding antagonist is a PD-1 binding antagonist. In some embodiments, the PD-1 axis binding antagonist is a PD-L1 binding antagonist. In some embodiments, the PD-1 axis binding antagonist is a PD-L2 binding antagonist.

In some embodiments of any of the methods, the method further comprises administering to the subject a glucocorticoid. In some embodiments, the glucocorticoid is dexamethasone.

In some embodiments of any of the methods, the method further comprises administering to the subject rituximab.

BRIEF DESCRIPTION OF THE FIGURES

FIG. 1A-C shows endogenous B cell killing with anti-CD79b/CD3 TDB (T cell dependent bispecific) antibodies produced in either K&H format or as bisfabs (various anti-CD79b clones paired with anti-CD3 clone UCHT1v9). 200,000 PBMCs were incubated with or without anti-CD79b TDB for 24 hours. At the end of the incubation, the number of live B cells was counted by gating on CD19+/PI- population. The percent of B cell killing was calculated as follows: (live B cell number without TDB—live B cell number with TDB)/(live B cell number without TDB)*100.

FIG. 2A-D shows B cell killing and T cell activation activity of bisfab anti-CD79b/CD3 (CD79b.A7/UCHT1v9). A and B: 200,000 PBMCs were incubated with or without anti-CD79b TDB for 24 h. At the end of the incubation, the number of live B cells was counted by gating on CD19+/PI-population. The percent of B cell killing (A) was calculated as follows: (live B cell number without TDB—live B cell number with TDB)/(live B cell number without TDB) *100; T cell activation (B) was measured by gating on CD69+/CD25+ cells in CD8+ T cell population. C and D: 20,000 BJAB cells and 100,000 CD8+ T cells were incubated with or without anti-CD79b TDB for 24 h. At the end of the incubation, the number of live B cells was counted by gating on CD19+/PI- population. The percent of B cell killing (C) was calculated as follows: (live B cell number without TDB—live B cell number with TDB)/(live B cell number without TDB)*100; T cell activation (D) was measured by gating on CD69+/CD25+ cells in CD8+ T cell population.

FIG. 3A-C shows monovalent or bivalent binding affinity of various clones of anti-CD79b measured by FACS. BJAB cells were incubated with anti-CD79b antibody (bivalent, dual arm antibody) or anti-CD79b/CD3 TDB antibody as indicated for 30 minutes on ice. At the end of the incubation, cells were washed with ice cold FACS buffer (1×PBS, 2% BSA, 2 mM EDTA), followed by incubation with PE-labeled mouse anti-human IgG antibody (BD bioscience #555787). Flow cytometry analysis was done on a BD LSR analyzer. Antibody binding was expressed as Mean Fluorescence Intensity (MFI) of PE fluorophore. A: The bivalent binding affinity of anti-CD79b clone 2F2 comparing to monovalent binding affinity of anti-CD79b clones 2F2, SN8v28, and SN8new (as K&H TDBs); B: bivalent binding affinity of anti-CD79b clones CD79b.F6 and CD79b.A7 comparing to monovalent binding of anti-CD79b clones CD79b.F6, CD79b.A7, and SN8v28 (as bisfab or K&H TDBs); C: bivalent binding affinity of anti-CD79b clone CD79b.A7.v14 comparing to monovalent binding of anti-CD79b clone CD79b.A7.v14 (as K&H TDBs).

Figure 4A:
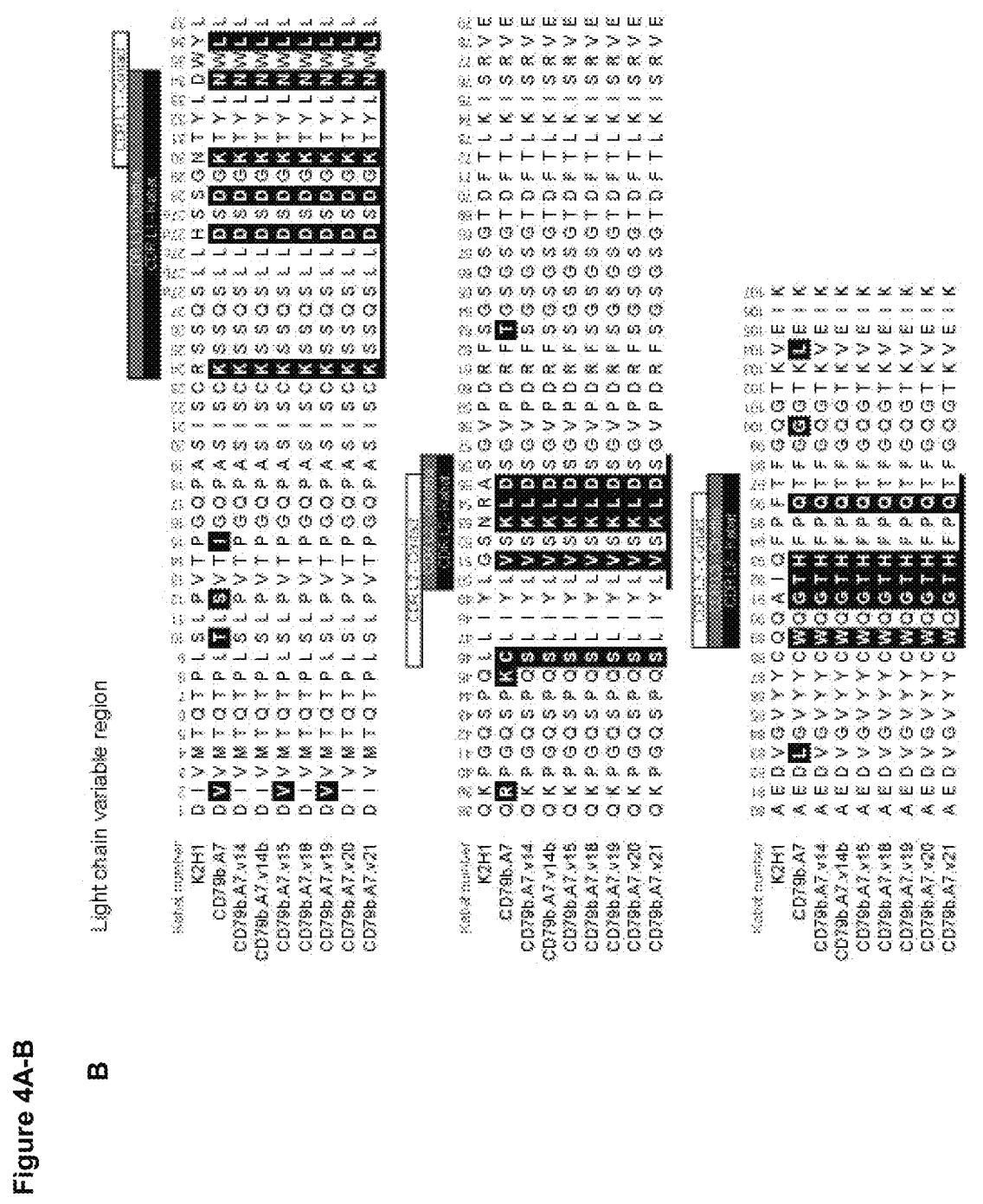

FIG. 4A-B shows alignment of (A) heavy chain variable region (SEQ ID NOS 13, 15, 17, 19, 21, 23, 25, 27 and 29, respectively, in order of appearance) and (B) light chain variable region (SEQ ID NOS 14, 16, 18, 20, 22, 24, 26, 28 and 30, respectively, in order of appearance) of CD79b antibody variants.

FIG. 5A-B shows B cell killing and T cell activation activity of anti-CD79b/CD3 TDBs (CD79b.A7.v14 paired with either anti-CD3 clone 40G5c or 38E4v1). 200,000 PBMCs were incubated with or without anti-CD79b TDB for 48 hours. At the end of the incubation, the number of live B cells was counted by gating on CD19+/PI- population. The percent of B cell killing (A) was calculated as follows: (live B cell number without TDB—live B cell number with TDB)/(live B cell number without TDB)*100; T cell activation (B) was measured by gating on CD69$^+$/CD25$^+$ cells in CD8$^+$ T cell population.

FIG. 6A-B shows B cell killing and T cell activation activity of anti-CD79b/CD3 TDBs (CD79b.A7v14/38E4v1). 20,000 BJAB or WSU-DLCL2 cells and 100,000 CD8+ T cells were incubated with or without anti-CD79b TDB for 48 hours. At the end of the incubation, the number of live B cells was counted by gating on CD19+/PI-population. The percent of B cell killing (A) was calculated as follows: (live B cell number without TDB—live B cell number with TDB)/(live B cell number without TDB)*100; T cell activation (B) was measured by gating on CD69+/CD25+ cells in CD8+ T cell population.

FIG. 7A-C shows B cell killing activity of anti-CD79b/CD3 TDB antibody (A7.v14b/38E4v1). 20,000 B lymphoma cells (as indicated) and 100,000 CD8+ T cells were incubated with or without anti-CD79b TDB for 48 hours. At the end of the incubation, the number of live B cells was counted by gating on CD19+/PI− population. The percent of B cell killing was calculated as follows: (live B cell number without TDB—live B cell number with TDB)/(live B cell number without TDB)*100. A. shows a dose response curve of B cell killing for BJAB, WSU-DLCL2, and OCI-LY-19 cells, with HT cells as CD79b negative control; B-C. show B cell killing with 5000 ng/ml Xanti-CD79 TDB (duplicate, average±STD).

FIG. 8A-B shows B cell killing activity of anti-CD79b/CD3 TDB antibody (CD79b.A7.v14b/38E4v1) in vitro and in vivo. BJAB cell variants (BJAB-CD79b ADC-R T1.1 and BJAB-SN8v28vcE CD79b ADC-R T1.2) were derived from non-responsive BJAB xenograft tumors in anti-CD79b-MC-vc-PAB-MMAE treated mice. A. shows dose response curve of BJAB cell killing in vitro: 20,000 BJAB or BJAB variant cells (as indicated) and 100,000 CD8+ T cells were incubated with or without anti-CD79b/CD3 TDB antibody (CD79b.A7.v14b/38E4v1) for 48 hours. At the end of the incubation, the number of live B cells was counted by gating on CD19+/PI− population. The percent of B cell killing was calculated as follows: (live B cell number without TDB—live B cell number with TDB)/(live B cell number without TDB)*100; B. anti-CD79b/CD3 TDB antibody (CD79b.A7.v14b/38E4v1) prevents BJAB tumor growth in vivo: BJAB cells and PBMCs from healthy donor were mixed and inoculated subcutaneously, and mice were then treated as indicated. Tumor volumes were measured throughout the study up to 42 days.

DETAILED DESCRIPTION OF EMBODIMENTS OF THE INVENTION

I. Definitions

The term "CD79b", as used herein, refers to any native CD79b from any vertebrate source, including mammals such as primates (e.g., humans, cynomologus monkey (cyno)) and rodents (e.g., mice and rats), unless otherwise indicated. Human CD79b is also referred herein to as "Igfβ," "B29," "DNA225786" or "PRO36249." An exemplary CD79b sequence including the signal sequence is shown in SEQ ID NO:1. An exemplary CD79b sequence without the signal sequence is shown in SEQ ID NO:2. The term "CD79b" encompasses "full-length," unprocessed CD79b as well as any form of CD79b that results from processing in the cell. The term also encompasses naturally occurring variants of CD79b, e.g., splice variants, allelic variants and isoforms. The CD79b polypeptides described herein may be isolated from a variety of sources, such as from human tissue types or from another source, or prepared by recombinant or synthetic methods. A "native sequence CD79b polypeptide" comprises a polypeptide having the same amino acid sequence as the corresponding CD79b polypeptide derived from nature. Such native sequence CD79b polypeptides can be isolated from nature or can be produced by recombinant or synthetic means. The term "native sequence CD79b polypeptide" specifically encompasses naturally-occurring truncated or secreted forms of the specific CD79b polypeptide (e.g., an extracellular domain sequence), naturally-occurring variant forms (e.g., alternatively spliced forms) and naturally-occurring allelic variants of the polypeptide.

The term "cluster of differentiation 3" or "CD3," as used herein, refers to any native CD3 from any vertebrate source, including mammals such as primates (e.g. humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI RefSeq No. NP_000724), which is 207 amino acids in length, and human CD3γ protein (NCBI RefSeq No. NP_000064), which is 182 amino acids in length.

The terms "anti-CD79b antibody" and "an antibody that binds to CD79b" refer to an antibody that is capable of binding CD79b with sufficient affinity such that the antibody is useful as a diagnostic and/or therapeutic agent in targeting CD79b. In one embodiment, the extent of binding of an anti-CD79b antibody to an unrelated, non-CD79b protein is less than about 10% of the binding of the antibody to CD79b as measured, e.g., by a radioimmunoassay (RIA). In certain embodiments, an antibody that binds to CD79b has a dissociation constant (Kd) of ≤1 μM, ≤100 nM, ≤10 nM, ≤1 nM, ≤0.1 nM, ≤0.01 nM, or ≤0.001 nM (e.g., $10^{-8}$M or less, e.g. from $10^{-8}$M to $10^{-13}$M, e.g., from $10^{-9}$M to $10^{-13}$ M). In certain embodiments, an anti-CD79b antibody binds to an epitope of CD79b that is conserved among CD79b from different species.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant (Kd) of ≤1 μM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$ M). In certain embodiments, an anti-CD3 antibody binds to an epitope of CD3 that is conserved among CD3 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The terms "full length antibody," "intact antibody," and "whole antibody" are used herein interchangeably to refer to an antibody having a structure substantially similar to a native antibody structure or having heavy chains that contain an Fc region as defined herein.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32(L1), 50-52 (L2), 91-96 (L3), 26-32(H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'2, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "immunoconjugate" is an antibody conjugated to one or more heterologous molecule(s), including but not limited to a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{186}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CD79b antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

"Isolated nucleic acid encoding an anti-CD3 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

An "effective amount" of an agent, e.g., a pharmaceutical formulation, refers to an amount effective, at dosages and for periods of time necessary, to achieve the desired therapeutic or prophylactic result. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, "delaying progression" of a disorder or disease means to defer, hinder, slow, retard, stabilize, and/or postpone development of the disease or disorder (e.g., a cell proliferative disorder, e.g., cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

By "reduce" or "inhibit" is meant the ability to cause an overall decrease, for example, of 20% or greater, of 50% or greater, or of 75%, 85%, 90%, 95%, or greater. In certain embodiments, reduce or inhibit can refer to the effector function of an antibody that is mediated by the antibody Fc region, such effector functions specifically including complement-dependent cytotoxicity (CDC). antibody-dependent cellular cytotoxicity (ADCC), and antibody-dependent cellular phagocytosis (ADCP).

A "chemotherapeutic agent" refers to a chemical compound useful in the treatment of cancer. Examples of chemotherapeutic agents include alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); Ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies including anti-interferon-alpha, -beta, or -gamma antibodies, anti-tumor necrosis factor(TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists (such as ACTEMRA™ (tocilizumab)); anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/ CD4a antibodies; soluble peptide containing a LFA-3 binding domain (WO 90/08187 published Jul. 26, 1990); streptokinase; transforming growth factor-beta (TGF-beta); streptodornase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., Science, 251: 430-432 (1991); WO 90/11294; Ianeway, Nature, 341: 482 (1989); and WO 91/01133); BAFF antagonists such as BAFF antibodies and BR3 antibodies and zTNF4 antagonists (for review, see Mackay and Mackay, Trends Immunol., 23:113-5 (2002) and see also definition below); biologic agents that interfere with T cell helper signals, such as anti-CD40 receptor or anti-CD40 ligand (CD154), including blocking antibodies to CD40-CD40 ligand (e.g., Durie et al., Science, 261: 1328-30 (1993); Mohan et al., J. Immunol., 154: 1470-80 (1995)) and CTLA4-Ig (Finck et al., Science, 265: 1225-7 (1994)); and T-cell receptor antibodies (EP 340,109) such as T10B9. Some preferred immunosuppressive agents herein include cyclophosphamide, chlorambucil, azathioprine, leflunomide, MMF, or methotrexate.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (lambrolizumab) described herein. In another specific aspect, a PD-1 binding antagonist is CT-011 (pidilizumab) described herein. In another specific aspect, a PD-1 binding antagonist is AMP-224 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.870 described herein. In another specific aspect, an anti-PD-L1 antibody is MDX-1105 described herein. In still another specific aspect, an anti-PD-L1 antibody is MPDL3280A described herein. In still another specific aspect, an anti-PD-L1 antibody is MEDI4736 described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cell proliferative disorder" and "proliferative disorder" refer to disorders that are associated with some degree of abnormal cell proliferation. In one embodiment, the cell proliferative disorder is cancer.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia.

The terms "B cell proliferative disorder" refer to disorders that are associated with some degree of abnormal B cell proliferation. In one embodiment, the B cell proliferative disorder is cancer.

"B-cell proliferative disorder" include Hodgkin's disease including lymphocyte predominant Hodgkin's disease (LPHD); non-Hodgkin's lymphoma (NHL); follicular center cell (FCC) lymphomas; acute lymphocytic leukemia (ALL); chronic lymphocytic leukemia (CLL); and Hairy cell leukemia. The non-Hodgkins lymphoma include low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, plasmacytoid lymphocytic lymphoma, mantle cell lymphoma, AIDS-related lymphoma and Waldenstrom's macroglobulinemia. Treatment of relapses of these cancers are also contemplated. LPHD is a type of Hodgkin's disease that tends to relapse frequently despite radiation or chemotherapy treatment. CLL is one of four major types of leukemia. A cancer of mature B cells called lymphocytes, CLL is manifested by progressive accumulation of cells in blood, bone marrow and lymphatic tissues. Indolent lymphoma is a slow-growing, incurable disease in which the average patient survives between six and 10 years following numerous periods of remission and relapse.

The term "non-Hodgkin's lymphoma" or "NHL", as used herein, refers to a cancer of the lymphatic system other than Hodgkin's lymphomas. Hodgkin's lymphomas can generally be distinguished from non-Hodgkin's lymphomas by the presence of Reed-Sternberg cells in Hodgkin's lymphomas and the absence of said cells in non-Hodgkin's lymphomas. Examples of non-Hodgkin's lymphomas encompassed by the term as used herein include any that would be identified as such by one skilled in the art (e.g., an oncologist or pathologist) in accordance with classification schemes known in the art, such as the Revised European-American Lymphoma (REAL) scheme as described in Color Atlas of Clinical Hematology, Third Edition; A. Victor Hoffbrand and John E. Pettit (eds.) (Harcourt Publishers Limited 2000) (see, in particular FIG. 11.57, 11.58 and/or 11.59). More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B cell chronic lymphacytic leukemia and/or prolymphocytic leukemia and/or small lymphocytic lymphoma, B-cell prolymphocytic lymphoma, immunocytoma and/or lymphoplasmacytic lymphoma, marginal zone B cell lymphoma, splenic marginal zone lymphoma, extranodal marginal zone—MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) T-cell lymphoblastic leukemia and/or lymphoma, adult T-cell lymphoma and/or leukemia, T cell chronic lymphocytic leukemia and/or prolymphacytic leukemia, large granular lymphocytic leukemia, mycosis fungoides and/or Sezary syndrome, extranodal natural killer/T-cell (nasal type) lymphoma, enteropathy type T-cell lymphoma, hepatosplenic T-cell lymphoma, subcutaneous panniculitis like T-cell lymphoma, skin (cutaneous) lymphomas, anaplastic large cell lymphoma, angiocentric lymphoma, intestinal T cell lymphoma, peripheral T-cell (not otherwise specified) lymphoma and angioimmunoblastic T-cell lymphoma.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X".

It is understood that aspects and variations of the invention described herein include "consisting of" and/or "consisting essentially of" aspects and variations.

II. Compositions and Methods

In one aspect, the invention is based, in part, onanti-CD79b antibodies. In certain embodiments, the anti-CD79b antibodies comprising a CD79b binding domain and a CD3 binding domain are provided. In certain embodiments, the anti-CD79b antibodies are anti-CD79b T cell dependent bispecific (TDB) antibodies. Antibodies of the invention are useful, e.g., for the diagnosis or treatment of B cell proliferative diseases.

A. Exemplary Anti-CD79b Antibodies

In one aspect, the invention provides isolated antibodies that bind to CD79b. In some embodiments of any of the anti-CD79b antibodies, the CD79b binding domain binds to SEQ ID NO:63.

In some embodiments of any of the anti-CD79b antibodies, the anti-CD79b antibody (e.g., CD79b binding domain) binds human CD79b with a Kd of less than about 25 nM as a dual arm, bivalent IgG antibody. In some embodiments of any of the anti-CD79b antibodies, the anti-CD79b antibody (e.g., CD79b binding domain) binds human CD79b with a Kd of less than about 10 nM. In some embodiments of any of the anti-CD79b antibodies, the anti-CD79b antibody (e.g., CD79b binding domain) binds human CD79b with a Kd of less than about 5 nM. In some embodiments, the Kd is determined by any method described herein, in particular the examples. In some embodiments, Kd is determined by BIACORE. In some embodiments, Kd is determined by CD79b immobilized at a low density.

In some embodiments of any of the anti-CD79b antibodies, the anti-CD79b antibody (e.g., CD79b binding domain) binds a B cell (e.g., BJAB cell) at an $EC_{50}$ of less than about 150 ng/mL as a dual arm, bivalent IgG antibody. In some embodiments, the $EC_{50}$ is less than about 100 ng/mL. In some embodiments, the $EC_{50}$ is less than about 75 ng/mL. In some embodiments, the $EC_{50}$ is less than about 50 ng/mL. In some embodiments, the $EC_{50}$ is determined by any method described herein, in particular the examples. In some embodiments, the $EC_{50}$ is the average about any of 5 or 10 experiments. In some embodiments, binding to a B cell is determined by FACS.

In some embodiments of any of the anti-CD79b antibodies, the anti-CD79b antibody (e.g., CD79b binding domain) binds human CD79b binds a B cell (e.g., BJAB cell) at an $EC_{50}$ of less than about 1.5 ug/mL in a monovalent format (e.g., an anti-CD79b bispecific antibody comprising a CD79b and CD3 binding domain. In some embodiments, the $EC_{50}$ is less than about 1 ug/mL. In some embodiments, the $EC_{50}$ is less than about 0.75 ug/mL. In some embodiments, the $EC_{50}$ is less than about 0.5 ug/mL. In some embodiments, the $EC_{50}$ is less than about 0.25 ug/mL. In some embodiments, the $EC_{50}$ is determined by any method described herein, in particular the examples. In some embodiments, the $EC_{50}$ is the average about any of 5 or 10 experiments. In some embodiments, binding to a B cell is determined by FACS.

Antibody CD79.A7 and Variants Thereof

In one aspect, the invention provides an anti-CD79b antibody comprising a CD79b binding domain comprising at least one, two, three, four, five, or six HVRs selected from (a) HVR-H1 comprising the amino acid sequence of SEQ ID NO:5; (b) HVR-H2 comprising the amino acid sequence of SEQ ID NO:8; (c) HVR-H3 comprising the amino acid sequence of SEQ ID NO:9; (d) HVR-L1 comprising the amino acid sequence of SEQ ID NO:10; (e) HVR-L2 comprising the amino acid sequence of SEQ ID NO:11; and (f) HVR-L3 comprising the amino acid sequence of SEQ ID NO:12. In some embodiments, HVR-H1 comprises the amino acid sequence of SEQ ID NO:3. In some embodiments, HVR-H1 comprises the amino acid sequence of SEQ ID NO:4. In some embodiments, HVR-H2 comprises the amino acid sequence of SEQ ID NO:6. In some embodiments, HVR-H2 comprises the amino acid sequence of SEQ ID NO:7.

In one aspect, the invention provides an anti-CD79b antibody comprising a CD79b binding domain comprising at least one, at least two, or all three VH HVR sequences selected from (a) HVR-H1 comprising the amino acid sequence of SEQ ID NO:5; (b) HVR-H2 comprising the amino acid sequence of SEQ ID NO:8; and (c) HVR-H3 comprising the amino acid sequence of SEQ ID NO:9. In one embodiment, the antibody comprises HVR-H3 comprising the amino acid sequence of SEQ ID NO:9. In another embodiment, the antibody comprises HVR-H3 comprising the amino acid sequence of SEQ ID NO:9 and HVR-L3 comprising the amino acid sequence of SEQ ID NO:12. In a further embodiment, the antibody comprises HVR-H3 comprising the amino acid sequence of SEQ ID NO:9, HVR-L3 comprising the amino acid sequence of SEQ ID NO:12, and HVR-H2 comprising the amino acid sequence of SEQ ID NO:8. In a further embodiment, the antibody comprises (a) HVR-H1 comprising the amino acid sequence of SEQ ID NO:5; (b) HVR-H2 comprising the amino acid sequence of SEQ ID NO:8; and (c) HVR-H3 comprising the amino acid sequence of SEQ ID NO:9. In some embodiments, HVR-H1 comprises the amino acid sequence of SEQ ID NO:3. In some embodiments, HVR-H1 comprises the amino acid sequence of SEQ ID NO:4. In some embodiments, HVR-H2 comprises the amino acid sequence of SEQ ID NO:6. In some embodiments, HVR-H2 comprises the amino acid sequence of SEQ ID NO:7. In a further embodiment, the antibody comprises (a) HVR-H1 comprising the amino acid sequence of SEQ ID NO:3; (b) HVR-H2 comprising the amino acid sequence of SEQ ID NO:6; and (c) HVR-H3 comprising the amino acid sequence of SEQ ID NO:9. In a further embodiment, the antibody comprises (a) HVR-H1 comprising the amino acid sequence of SEQ ID NO:4; (b) HVR-H2 comprising the amino acid sequence of SEQ ID NO:7; and (c) HVR-H3 comprising the amino acid sequence of SEQ ID NO:9.

In another aspect, the invention provides an anti-CD79b antibody comprising a CD79b binding domain comprising at least one, at least two, or all three VL HVR sequences selected from (a) HVR-L1 comprising the amino acid sequence of SEQ ID NO:10; (b) HVR-L2 comprising the amino acid sequence of SEQ ID NO:11; and (c) HVR-L3 comprising the amino acid sequence of SEQ ID NO:12. In one embodiment, the antibody comprises (a) HVR-L1 comprising the amino acid sequence of SEQ ID NO:10; (b) HVR-L2 comprising the amino acid sequence of SEQ ID NO:11; and (c) HVR-L3 comprising the amino acid sequence of SEQ ID NO:12.

In another aspect, an anti-CD79b antibody of the invention comprises CD79b binding domain comprising at (a) a VH domain comprising at least one, at least two, or all three VH HVR sequences selected from (i) HVR-H1 comprising the amino acid sequence of SEQ ID NO:5, (ii) HVR-H2 comprising the amino acid sequence of SEQ ID NO:8, and (iii) HVR-H3 comprising an amino acid sequence selected from SEQ ID NO:9; and (b) a VL domain comprising at least one, at least two, or all three VL HVR sequences selected from (i) HVR-L1 comprising the amino acid sequence of SEQ ID NO:10, (ii) HVR-L2 comprising the amino acid sequence of SEQ ID NO:11, and (c) HVR-L3 comprising the amino acid sequence of SEQ ID NO:12. In some embodiments, HVR-H1 comprises the amino acid sequence of SEQ ID NO:3. In some embodiments, HVR-H1 comprises the amino acid sequence of SEQ ID NO:4. In some embodiments, HVR-H2 comprises the amino acid sequence of SEQ ID NO:6. In some embodiments, HVR-H2 comprises the amino acid sequence of SEQ ID NO:7.

In another aspect, the invention provides an anti-CD79b antibody comprising a CD79b binding domain comprising (a) HVR-H1 comprising the amino acid sequence of SEQ ID NO:5; (b) HVR-H2 comprising the amino acid sequence of SEQ ID NO:8; (c) HVR-H3 comprising the amino acid sequence of SEQ ID NO:9; (d) HVR-L1 comprising the amino acid sequence of SEQ ID NO:10; (e) HVR-L2 comprising the amino acid sequence of SEQ ID NO:11; and (f) HVR-L3 comprising an amino acid sequence selected from SEQ ID NO:12. In another aspect, the invention provides an anti-CD79b antibody comprising a CD79b binding domain comprising (a) HVR-H1 comprising the amino acid sequence of SEQ ID NO:3; (b) HVR-H2 comprising the amino acid sequence of SEQ ID NO:6; (c) HVR-H3 comprising the amino acid sequence of SEQ ID NO:9; (d) HVR-L1 comprising the amino acid sequence of SEQ ID NO:10; (e) HVR-L2 comprising the amino acid sequence of SEQ ID NO:11; and (f) HVR-L3 comprising an amino acid sequence selected from SEQ ID NO:12. In another aspect, the invention provides an anti-CD79b antibody comprising a CD79b binding domain comprising (a) HVR-H1 comprising the amino acid sequence of SEQ ID NO:4; (b) HVR-H2 comprising the amino acid sequence of SEQ ID NO:7; (c) HVR-H3 comprising the amino acid sequence of SEQ ID NO:9; (d) HVR-L1 comprising the amino acid sequence of SEQ ID NO:10; (e) HVR-L2 comprising the amino acid sequence of SEQ ID NO:11; and (f) HVR-L3 comprising an amino acid sequence selected from SEQ ID NO:12.

In any of the above embodiments, an anti-CD79b antibody is humanized. In one embodiment, an anti-CD79b antibody comprises HVRs as in any of the above embodiments, and further comprises an acceptor human framework, e.g. a human immunoglobulin framework or a human consensus framework.

In another aspect, an anti-CD79b antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:15, 17, 19, 21, 23, 25, 27, and/or 29. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CD79b antibody comprising that sequence retains the ability to bind to CD79b. In certain embodiments, a total of 1 to 10 amino acids have been substituted, inserted and/or deleted in SEQ ID NO:15, 17, 19, 21, 23, 25, 27, and/or 29. In certain embodiments, substitutions, insertions, or deletions occur in regions outside the HVRs (i.e., in the FRs). Optionally, the anti-CD79b antibody comprises the VH sequence in SEQ ID NO:15, 17, 19, 21, 23, 25, 27, and/or 29, including post-translational modifications of that sequence. In a particular embodiment, the VH comprises one, two or three HVRs selected from: (a) HVR-H1 comprising the amino acid sequence of SEQ ID NO:5, (b) HVR-H2 comprising the amino acid sequence of SEQ ID NO:8, and (c) HVR-H3 comprising the amino acid sequence of SEQ ID NO:9.

In another aspect, an anti-CD79b antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:16, 18, 20, 22, 24, 26, 28, and/or 30. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CD79B antibody comprising that sequence retains the ability to bind to CD79b. In certain embodiments, a total of 1 to 10 amino acids have been substituted, inserted and/or deleted in SEQ ID NO:16, 18, 20, 22, 24, 26, 28, and/or 30. In certain embodiments, the substitutions, insertions, or deletions occur in regions outside the HVRs (i.e., in the FRs). Optionally, the anti-CD79b antibody comprises the VL sequence in SEQ ID NO:16, 18, 20, 22, 24, 26, 28, and/or 30, including post-translational modifications of that sequence. In a particular embodiment, the VL comprises one, two or three HVRs selected from (a) HVR-L1 comprising the amino acid sequence of SEQ ID NO:10; (b) HVR-L2 comprising the amino acid sequence of SEQ ID NO:11; and (c) HVR-L3 comprising the amino acid sequence of SEQ ID NO:12.

In another aspect, an anti-CD79b antibody is provided, wherein the antibody comprises a VH as in any of the embodiments provided above, and a VL as in any of the embodiments provided above. In one embodiment, the antibody comprises the VH and VL sequences in SEQ ID NO:15 and SEQ ID NO:16, respectively, including post-translational modifications of those sequences. In one embodiment, the antibody comprises the VH and VL sequences in SEQ ID NO:17 and SEQ ID NO:18, respectively, including post-translational modifications of those sequences. In one embodiment, the antibody comprises the VH and VL sequences in SEQ ID NO:19 and SEQ ID NO:20, respectively, including post-translational modifications of those sequences. In one embodiment, the antibody comprises the VH and VL sequences in SEQ ID NO:21 and SEQ ID NO:22, respectively, including post-translational modifications of those sequences. In one embodiment, the antibody comprises the VH and VL sequences in SEQ ID NO:23 and SEQ ID NO:24, respectively, including post-translational modifications of those sequences. In one embodiment, the antibody comprises the VH and VL sequences in SEQ ID NO:25 and SEQ ID NO:26, respectively, including post-translational modifications of those sequences. In one embodiment, the antibody comprises the VH and VL sequences in SEQ ID NO:27 and SEQ ID NO:28, respectively, including post-translational modifications of those sequences. In one embodiment, the antibody comprises the VH and VL sequences in SEQ ID NO:29 and SEQ ID NO:30, respectively, including post-translational modifications of those sequences.

In a further aspect, the invention provides an antibody that binds to the same epitope as an anti-CD79b antibody provided herein. For example, in certain embodiments, an antibody is provided that binds to the same epitope as an anti-CD79b antibody comprising a VH sequence of SEQ ID NO:19 and a VL sequence of SEQ ID NO:20. In certain embodiments, an antibody is provided that binds to an epitope within a fragment of CD79b consisting of amino acids of SEQ ID NO:63.

In a further aspect of the invention, an anti-CD79b antibody according to any of the above embodiments is a monoclonal antibody, including a chimeric, humanized or human antibody. In one embodiment, an anti-CD79b antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

Antibody SN8.New and Variants Thereof

In one aspect, the invention provides an anti-CD79b antibody comprising a CD79b binding domain comprising at least one, two, three, four, five, or six HVRs selected from (a) HVR-H1 comprising the amino acid sequence of SEQ ID NO:31; (b) HVR-H2 comprising the amino acid sequence of SEQ ID NO:32; (c) HVR-H3 comprising the amino acid sequence of SEQ ID NO:33; (d) HVR-L1 comprising the amino acid sequence of SEQ ID NO:34; (e) HVR-L2 comprising the amino acid sequence of SEQ ID NO:35; and (f) HVR-L3 comprising the amino acid sequence of SEQ ID NO:36.

In one aspect, the invention provides an anti-CD79b antibody comprising a CD79b binding domain comprising at least one, at least two, or all three VH HVR sequences selected from (a) HVR-H1 comprising the amino acid sequence of SEQ ID NO:31; (b) HVR-H2 comprising the amino acid sequence of SEQ ID NO:32; and (c) HVR-H3 comprising the amino acid sequence of SEQ ID NO:33. In one embodiment, the antibody comprises HVR-H3 comprising the amino acid sequence of SEQ ID NO:33. In another embodiment, the antibody comprises HVR-H3 comprising the amino acid sequence of SEQ ID NO:33 and HVR-L3 comprising the amino acid sequence of SEQ ID NO:36. In a further embodiment, the antibody comprises HVR-H3 comprising the amino acid sequence of SEQ ID NO:33, HVR-L3 comprising the amino acid sequence of SEQ ID NO:36, and HVR-H2 comprising the amino acid sequence of SEQ ID NO:32. In a further embodiment, the antibody comprises (a) HVR-H1 comprising the amino acid sequence of SEQ ID NO:31; (b) HVR-H2 comprising the amino acid sequence of SEQ ID NO:32; and (c) HVR-H3 comprising the amino acid sequence of SEQ ID NO:33.

In another aspect, the invention provides an anti-CD79b antibody comprising a CD79b binding domain comprising at least one, at least two, or all three VL HVR sequences selected from (a) HVR-L1 comprising the amino acid sequence of SEQ ID NO:34; (b) HVR-L2 comprising the amino acid sequence of SEQ ID NO:35; and (c) HVR-L3 comprising the amino acid sequence of SEQ ID NO:36. In one embodiment, the antibody comprises (a) HVR-L1 comprising the amino acid sequence of SEQ ID NO:34; (b) HVR-L2 comprising the amino acid sequence of SEQ ID NO:35; and (c) HVR-L3 comprising the amino acid sequence of SEQ ID NO:36.

In another aspect, an anti-CD79b antibody of the invention comprises CD79b binding domain comprising at (a) a VH domain comprising at least one, at least two, or all three VH HVR sequences selected from (i) HVR-H1 comprising the amino acid sequence of SEQ ID NO:31, (ii) HVR-H2 comprising the amino acid sequence of SEQ ID NO:32, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:34, (ii) HVR-L2 comprising the amino acid sequence of SEQ ID NO:35, and (c) HVR-L3 comprising the amino acid sequence of SEQ ID NO:36.

In another aspect, the invention provides an anti-CD79b antibody comprising a CD79b binding domain comprising (a) HVR-H1 comprising the amino acid sequence of SEQ ID NO:31; (b) HVR-H2 comprising the amino acid sequence of SEQ ID NO:32; (c) HVR-H3 comprising the amino acid sequence of SEQ ID NO:33; (d) HVR-L1 comprising the amino acid sequence of SEQ ID NO:34; (e) HVR-L2 comprising the amino acid sequence of SEQ ID NO:35; and (f) HVR-L3 comprising an amino acid sequence selected from SEQ ID NO:36.

In any of the above embodiments, an anti-CD79b antibody is humanized. In one embodiment, an anti-CD79b antibody comprises HVRs as in any of the above embodiments, and further comprises an acceptor human framework, e.g. a human immunoglobulin framework or a human consensus framework.

In another aspect, an anti-CD79b antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:37. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CD79b antibody comprising that sequence retains the ability to bind to CD79b. In certain embodiments, a total of 1 to 10 amino acids have been substituted, inserted and/or deleted in SEQ ID NO:37. In certain embodiments, substitutions, insertions, or deletions occur in regions outside the HVRs (i.e., in the FRs). Optionally, the anti-CD79b antibody comprises the VH sequence in SEQ ID NO:37, including post-translational modifications of that sequence. In a particular embodiment, the VH comprises one, two or three HVRs selected from: (a) HVR-H1 comprising the amino acid sequence of SEQ ID NO:31, (b) HVR-H2 comprising the amino acid sequence of SEQ ID NO:32, and (c) HVR-H3 comprising the amino acid sequence of SEQ ID NO:33.

In another aspect, an anti-CD79b antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:38. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CD79B antibody comprising that sequence retains the ability to bind to CD79b. In certain embodiments, a total of 1 to 10 amino acids have been substituted, inserted and/or deleted in SEQ ID NO:38. In certain embodiments, the substitutions, insertions, or deletions occur in regions outside the HVRs (i.e., in the FRs). Optionally, the anti-CD79b antibody comprises the VL sequence in SEQ ID NO:38, including post-translational modifications of that sequence. In a particular embodiment, the VL comprises one, two or three HVRs selected from (a) HVR-L1 comprising the amino acid sequence of SEQ ID NO:34; (b) HVR-L2 comprising the amino acid sequence of SEQ ID NO:35; and (c) HVR-L3 comprising the amino acid sequence of SEQ ID NO:36.

In another aspect, an anti-CD79b antibody is provided, wherein the antibody comprises a VH as in any of the embodiments provided above, and a VL as in any of the embodiments provided above. In one embodiment, the antibody comprises the VH and VL sequences in SEQ ID NO:37 and SEQ ID NO:38, respectively, including post-translational modifications of those sequences.

In a further aspect of the invention, an anti-CD79b antibody according to any of the above embodiments is a monoclonal antibody, including a chimeric, humanized or human antibody. In one embodiment, an anti-CD79b antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, anti-CD79b antibodies according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., *J. Mol. Biol.* 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sri, USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for CD79b and the other is for any other antigen. In certain embodiments, bispecific antibodies may bind to two different epitopes of CD79b. Bispecific antibodies may also be used to localize cytotoxic agents to cells which express CD79b. Bispecific antibodies can be prepared as full length antibodies or antibody fragments.

In one aspect, the invention provides isolated anti-CD79b antibodies that bind to CD79b and CD3 (i.e., comprising a CD79b binding domain and a CD3 binding domain). In certain embodiments, one of the binding specificities is for CD3 (e.g., CD3ε or CD3γ) and the other is CD79b. In some embodiments, the CD3 binding domain binds to a human CD3 polypeptide or a cynomolgus monkey (cyno) CD3 polypeptide. In some embodiments, the human CD3 polypeptide or the cyno CD3 polypeptide is a human CD3ε polypeptide or a cyno CD3ε polypeptide, respectively. In some embodiments, the human CD3 polypeptide or the cyno CD3 polypeptide is a human CD3γ polypeptide or a cyno CD3γ polypeptide, respectively. In certain embodiments, an anti-CD79b antibody is provided comprising a CD3 binding domain which binds to an epitope within a fragment of CD3 (e.g., human CD3ε) consisting of amino acids 1-26 or 1-27 of human CD3ε. In some embodiments, the anti-CD79b antibody is a bispecific antibody. In some embodiments, the anti-CD79b antibody is a bispecific IgG antibody.

In some embodiments, CD3 binding domain binds the human CD3ε polypeptide with a Kd of 250 nM or lower. In some embodiments, the CD3 binding domain binds the human CD3ε polypeptide with a Kd of 100 nM or lower. In some embodiments, the CD3 binding domain binds the human CD3ε polypeptide with a Kd of 15 nM or lower. In some embodiments, CD3 binding domain binds the human CD3ε polypeptide with a Kd of 10 nM or lower. In some embodiments, CD3 binding domain binds the human CD3ε polypeptide with a Kd of 5 nM or lower.

In some embodiments of any of the multispecific antibodies, e.g., a bispecific antibody, that bind to CD79b and CD3, comprises a CD3 binding domain, wherein the CD3 binding domain comprises the hypervariable regions (HVRs) (a) HVR-H1 comprising the amino acid sequence of SEQ ID NO:39; (b) HVR-H2 comprising the amino acid sequence of SEQ ID NO:40; (c) HVR-H3 comprising the amino acid sequence of SEQ ID NO:41; (d) HVR-L1 comprising the amino acid sequence of SEQ ID NO:42; (e) HVR-L2 comprising the amino acid sequence of SEQ ID NO:43; and (f) HVR-L3 comprising the amino acid sequence of SEQ ID NO:44. In some embodiments, the CD3 binding domain comprises (a) a VH domain comprising (i) HVR-H1 comprising the amino acid sequence of SEQ ID NO:39, (ii) HVR-H2 comprising the amino acid sequence of SEQ ID NO:40, and (iii) HVR-H3 comprising an amino acid sequence selected from SEQ ID NO:41; and (b) a VL domain comprising (i) HVR-L1 comprising the amino acid sequence of SEQ ID NO:42, (ii) HVR-L2 comprising the amino acid sequence of SEQ ID NO:43, and (iii) HVR-L3 comprising the amino acid sequence of SEQ ID NO:44. In some instances, the CD3 binding domain may have a heavy chain variable (VH) domain including an amino acid sequence having at least 90% sequence identity (e.g., at least 91%, 92%, 93%, 94%, 95%, 96%, 97%, 98%, or 99% sequence identity) to, or the sequence of, SEQ ID NO:57 and/or a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:58. In some instances, the CD3 binding domain may have a VH domain comprising the amino acid sequence of SEQ ID NO:57 and a VL domain comprising the amino acid sequence of SEQ ID NO:58. In a particular instance, the CD3 binding domain can be 40G5c, or a derivative or clonal relative thereof.

For example, in some embodiments, the anti-CD79b antibody comprises (i) a CD79b binding domain comprising the HVRs (a) HVR-H1 comprising the amino acid sequence of SEQ ID NO:4; (b) HVR-H2 comprising the amino acid sequence of SEQ ID NO:7; (c) HVR-H3 comprising the amino acid sequence of SEQ ID NO:9; (d) HVR-L1 comprising the amino acid sequence of SEQ ID NO:10; (e) HVR-L2 comprising the amino acid sequence of SEQ ID NO:11; and (f) HVR-L3 comprising the amino acid sequence of SEQ ID NO:12 and (ii) a CD3 binding domain comprising the HVRs (a) HVR-H1 comprising the amino acid sequence of SEQ ID NO:39; (b) HVR-H2 comprising the amino acid sequence of SEQ ID NO:40; (c) HVR-H3 comprising the amino acid sequence of SEQ ID NO:41; (d) HVR-L1 comprising the amino acid sequence of SEQ ID NO:42; (e) HVR-L2 comprising the amino acid sequence of SEQ ID NO:43; and (f) HVR-L3 comprising the amino acid sequence of SEQ ID NO:44. In some embodiments, the anti-CD79b antibody comprises (i) a CD79b binding domain comprising (a) a VH domain comprising the amino acid sequence of SEQ ID NO:19 and (b) a VL domain comprising the amino acid sequence of SEQ ID NO:20 and (ii) a CD3 binding domain comprising (a) a VH domain comprising the amino acid sequence of SEQ ID NO:57 and (b) a VL domain comprising the amino acid sequence of SEQ ID NO:58.

In some embodiments of any of the multispecific antibodies, e.g. a bispecific antibody, that bind to CD79b and CD3, the CD3 binding domain comprises (a) HVR-H1 comprising the amino acid sequence of SEQ ID NO:45; (b) HVR-H2 comprising the amino acid sequence of SEQ ID NO:46; (c) HVR-H3 comprising the amino acid sequence of SEQ ID NO:47; (d) HVR-L1 comprising the amino acid sequence of SEQ ID NO:48; (e) HVR-L2 comprising the amino acid sequence of SEQ ID NO:49; and (f) HVR-L3 comprising the amino acid sequence of SEQ ID NO:50. In some embodiments, the CD3 binding domain comprises (a) a VH domain comprising (i) HVR-H1 comprising the amino acid sequence of SEQ ID NO:45, (ii) HVR-H2 comprising the amino acid sequence of SEQ ID NO:46, and (iii) HVR-H3 comprising an amino acid sequence selected from SEQ ID NO:47; and (b) a VL domain comprising (i) HVR-L1 comprising the amino acid sequence of SEQ ID NO:48, (ii) HVR-L2 comprising the amino acid sequence of SEQ ID NO:49, and (iii) HVR-L3 comprising the amino acid sequence of SEQ ID NO:50. In some instances, the CD3 binding domain may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:59 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:60. In some instances, the CD3 binding domain may have a VH domain comprising the amino acid sequence of SEQ ID NO:59 and a VL domain comprising the amino acid sequence of SEQ ID NO:60. In a particular instance, the CD3 binding domain can be 38E4v1, or a derivative or clonal relative thereof.

For example, in some embodiments, the anti-CD79b antibody comprises (i) a CD79b binding domain comprising the HVRs (a) HVR-H1 comprising the amino acid sequence of SEQ ID NO:4; (b) HVR-H2 comprising the amino acid sequence of SEQ ID NO:7; (c) HVR-H3 comprising the amino acid sequence of SEQ ID NO:9; (d) HVR-L1 comprising the amino acid sequence of SEQ ID NO:10; (e) HVR-L2 comprising the amino acid sequence of SEQ ID NO:11; and (f) HVR-L3 comprising the amino acid sequence of SEQ ID NO:12 and (ii) a CD3 binding domain comprising the HVRs (a) HVR-H1 comprising the amino acid sequence of SEQ ID NO:45; (b) HVR-H2 comprising the amino acid sequence of SEQ ID NO:46; (c) HVR-H3 comprising the amino acid sequence of SEQ ID NO:47; (d) HVR-L1 comprising the amino acid sequence of SEQ ID NO:48; (e) HVR-L2 comprising the amino acid sequence of SEQ ID NO:49; and (f) HVR-L3 comprising the amino acid sequence of SEQ ID NO:50. In some embodiments, the anti-CD79b antibody comprises (i) a CD79b binding domain comprising (a) a VH domain comprising the amino acid sequence of SEQ ID NO:19 and (b) a VL domain comprising the amino acid sequence of SEQ ID NO:20 and (ii) a CD3 binding domain comprising (a) a VH domain comprising the amino acid sequence of SEQ ID NO:59 and (b) a VL domain comprising the amino acid sequence of SEQ ID NO:60.

In some embodiments of any of the multispecific antibodies, e.g. a bispecific antibody, that bind to CD79b and CD3, the CD3 binding domain comprises from (a) HVR-H1 comprising the amino acid sequence of SEQ ID NO:51; (b) HVR-H2 comprising the amino acid sequence of SEQ ID NO:52; (c) HVR-H3 comprising the amino acid sequence of SEQ ID NO:53; (d) HVR-L1 comprising the amino acid sequence of SEQ ID NO:54; (e) HVR-L2 comprising the amino acid sequence of SEQ ID NO:55; and (f) HVR-L3 comprising the amino acid sequence of SEQ ID NO:56. In some embodiments, the CD3 binding domain comprises (a) a VH domain comprising (i) HVR-H1 comprising the amino acid sequence of SEQ ID NO:51, (ii) HVR-H2 comprising the amino acid sequence of SEQ ID NO:52, and (iii) HVR-H3 comprising an amino acid sequence selected from SEQ ID NO:53; and (b) a VL domain comprising (i) HVR-L1 comprising the amino acid sequence of SEQ ID NO:54, (ii) HVR-L2 comprising the amino acid sequence of SEQ ID NO:55, and (iii) HVR-L3 comprising the amino acid sequence of SEQ ID NO:56. In some instances, the anti-CD3 antibody may have a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:61 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:62. In some instances, the CD3 binding domain may have a VH domain comprising the amino acid sequence of SEQ ID NO:61 and a VL domain comprising the amino acid sequence of SEQ ID NO:62. In a particular instance, the anti-CD3 antibody can be UCHT1.v9, or a derivative or clonal relative thereof.

For example, in some embodiments, the anti-CD79b antibody comprises (i) a CD79b binding domain comprising the HVRs (a) HVR-H1 comprising the amino acid sequence of SEQ ID NO:4; (b) HVR-H2 comprising the amino acid sequence of SEQ ID NO:7; (c) HVR-H3 comprising the amino acid sequence of SEQ ID NO:9; (d) HVR-L1 comprising the amino acid sequence of SEQ ID NO:10; (e) HVR-L2 comprising the amino acid sequence of SEQ ID NO:11; and (f) HVR-L3 comprising the amino acid sequence of SEQ ID NO:12 and (ii) a CD3 binding domain comprising the HVRs (a) HVR-H1 comprising the amino acid sequence of SEQ ID NO:51; (b) HVR-H2 comprising the amino acid sequence of SEQ ID NO:52; (c) HVR-H3 comprising the amino acid sequence of SEQ ID NO:53; (d) HVR-L1 comprising the amino acid sequence of SEQ ID NO:54; (e) HVR-L2 comprising the amino acid sequence of SEQ ID NO:55; and (f) HVR-L3 comprising the amino acid sequence of SEQ ID NO:56. In some embodiments, the anti-CD79b antibody comprises (i) a CD79b binding domain comprising (a) a VH domain comprising the amino acid sequence of SEQ ID NO:19 and (b) a VL domain comprising the amino acid sequence of SEQ ID NO:20 and (ii) a CD3 binding domain comprising (a) a VH domain comprising the amino acid sequence of SEQ ID NO:61 and (b) a VL domain comprising the amino acid sequence of SEQ ID NO:62.

In some embodiments of any of the multispecific anti-CD79b antibodies, the anti-CD79b antibody has a B cell killing $EC_{50}$ of less than about 100 ng/mL. In some embodiments, the $EC_{50}$ is less than about 50 ng/mL. In some embodiments, the $EC_{50}$ is less than about 25 ng/mL. In some embodiments, the $EC_{50}$ is less than about 20 ng/mL. In some embodiments, the $EC_{50}$ is less than about 15 ng/mL. In some embodiments, the B cell killing is endogenous B cell killing. In some embodiments, the B cell killing is cell line B cell killing, e.g., BJAB cell line, WSU-CLCL2 cell line, OCI-Ly-19 cell line. In some embodiments, the $EC_{50}$ is determined by any method described herein, in particular the examples. In some embodiments, the $EC_{50}$ is the average of about any of 5 or 10 experiments. In some embodiments, the $EC_{50}$ is the average of about any of 5 or 10 donors.

In some embodiments of any of the multispecific anti-CD79b antibodies, the anti-CD79b antibody kills at least about 60% of B cells at 5000 ng/mL. In some embodiments, the anti-CD79b antibody kills at least about 80% of B cells at 5000 ng/mL. the anti-CD79b antibody kills at least about 90% of B cells at 5000 ng/mL. For example, in some embodiments, the B cells are one or more of the B cell lines SU-CHL-6, CoHH2, BJAB, WSU-DLCL2, Sc-1, SU-CHL-8, GRANTA-519, Nalm-6, Ramos, and/or OCI-Ly-19. In some embodiments, the $EC_{50}$ is determined by any method described herein, in particular the examples. In some embodiments, the $EC_{50}$ is the average of about any of 5 or 10 experiments. In some embodiments, the $EC_{50}$ is the average of about any of 5 or 10 donors.

In some embodiments of any of the multispecific anti-CD79b antibodies, the anti-CD79b antibody has a cytotoxic T cell activation $EC_{50}$ is less than about any of 50 ng/mL. In some embodiments, the anti-CD79b antibody has a cytotoxic T cell activation $EC_{50}$ is less than about 25 ng/mL. In some embodiments, the anti-CD79b antibody has a cytotoxic T cell activation $EC_{50}$ is less than about less than 20 ng/mL. In some embodiments, cytotoxic T cell activation is measured by % of CD69+CD25+ T cells in CD8+ T cells. In some embodiments, the $EC_{50}$ is determined by any method described herein, in particular the examples. In some embodiments, the $EC_{50}$ is the average of about any of 5 or 10 experiments. In some embodiments, the $EC_{50}$ is the average of about any of 5 or 10 donors.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see,e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to CD79b as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In some aspects the anti-CD79b antibody (e.g., anti-CD79b TDB antibody) comprises an Fc region comprising an N297G mutation.

In some embodiments, the anti-CD79b antibody comprising the N297G mutation comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some instances, at least one of the one or more heavy chain constant domains is paired with another heavy chain constant domain. In some instances, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some instances, the $CH3_1$ and $CH3_2$ domains meet at an interface between said protuberance and cavity. In some instances, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In other instances, the $CH2_1$ and $CH2_2$ domains meet at an interface between said protuberance and cavity. In some instances, the anti-CD3 antibody is an IgG1 antibody.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-CD79b antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CD79b antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD79b antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-CD79b antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with an anti-CD79b antibody described herein for binding to CD79b. In certain embodiments, such a competing antibody binds to the same epitope (e.g., a linear or a conformational epitope) that is bound by an anti-CD79b antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized CD79b is incubated in a solution comprising a first labeled antibody that binds to CD79b (e.g., an anti-CD79b antibody described herein) and a second unlabeled antibody that is being tested for its ability to compete with the first antibody for binding to CD79b. The second antibody may be present in a hybridoma supernatant. As a control, immobilized CD79b is incubated in a solution comprising the first labeled antibody but not the second unlabeled antibody. After incubation under conditions permissive for binding of the first antibody to CD79b, excess unbound antibody is removed, and the amount of label associated with immobilized CD79b is measured. If the amount of label associated with immobilized CD79b is substantially reduced in the test sample relative to the control sample, then that indicates that the second antibody is competing with the first antibody for binding to CD79b. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-CD79b antibodies (e.g., anti-CD79b/CD3 TDB antibody) thereof having biological activity. Biological activity may include, e.g., the ability to inhibit cell growth or proliferation (e.g., "cell killing" activity), the ability to induce cell death, including programmed cell death (apoptosis), or antigen binding activity. Antibodies having such biological activity in vivo and/or in vitro are also provided.

In some embodiments, the activity comprises ability to support B cell killing and/or the activation of the cytotoxic T cells. In certain embodiments, an anti-CD79b antibody (e.g., anti-CD79b/CD3 TDB antibody) of the invention is tested for such B cell killing and/or the activation of the cytotoxic effect of T cells biological activity by any of the methods described herein, in particular the Examples. In some embodiments of any of these activity assays, PBMCs may be isolated from whole blood of healthy donors by Ficoll separation. In particular, human blood may be collected in heparinized syringes, and PBMC were isolated using Leucosep and Ficoll Paque Plus. If needed CD4+T and CD8+ T cells may be separated with Miltenyi kits according to manufacturer's instructions.

Further, cells may be washed in RPMI medium containing 10% FBS, supplemented with GlutaMax, penicillin & streptomycin, and ~0.2 million suspended cells were added to a 96-well U-bottom plate. Cells may be cultured in RPMI1640 supplemented with 10% FBS at 37° C. in a humidified standard cell culture incubator. For BJAB cell killing assays, 20,000 BJAB cells may be incubated with effector cells either as huPBMCs or purified T cells as indicated ratios per assay, in the presence of various concentrations of TDB antibodies for 24 hours. For endogenous B cell killing assays, 200,000 huPBMCs may be incubated with various concentrations of TDB antibodies for 24 hours.

After culturing, cells may be washed with FACS buffer (0.5% BSA, 0.05% Na Azide in PBS). Cells may then be stained in FACS buffer, washed with FACS buffer and suspend in 100 ul of FACS buffer containing 1 ug/ml Propidium Iodide. Data may be collected on a FACSCalibur flow cytometer and analyzed using FlowJo. Live B cells may be gated out as PI-CD19+ or PI-CD20+ B cells by FACS, and absolute cell count may be obtained with FITC beads added to reaction mix as internal counting control. % of cell killing may be calculated based on non-TDB treated controls. Activated T cells may be detected by CD69 and CD25 surface expression using anti-CD69-FITC and anti-CD25-PE.

D. Immunoconjugates

The invention also provides immunoconjugates comprising an anti-CD79b antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include At$^{211}$, I$^{131}$, I$^{125}$, Y$^{90}$, Re$^{186}$, Re$^{186}$, Sm$^{153}$, Bi$^{212}$, P$^{32}$, Pb$^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In one aspect, anti-CD79b antibodies of the invention are useful for detecting the presence of CD79b in a biological sample. The term "detecting" as used herein encompasses quantitative or qualitative detection. In certain embodiments, a biological sample comprises a cell or tissue. In certain embodiments, such tissues include normal and/or cancerous tissues that express CD79b at higher levels relative to other tissues, for example, B cells and/or B cell associated tissues.

In one embodiment, an anti-CD79b antibody for use in a method of diagnosis or detection is provided. In a further aspect, a method of detecting the presence of CD79b in a biological sample is provided. In certain embodiments, the method comprises contacting the biological sample with an anti-CD79b antibody as described herein under conditions permissive for binding of the anti-CD79b antibody to CD79b, and detecting whether a complex is formed between the anti-CD79b antibody and CD79b. Such method may be an in vitro or in vivo method. In one embodiment, an anti-CD79b antibody is used to select subjects eligible for therapy with an anti-CD79b antibody, e.g. where CD79b is a biomarker for selection of patients.

Exemplary cell proliferative disorders that may be diagnosed using an antibody of the invention include a B cell disorder and/or a B cell proliferative disorder including, but not limited to, lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

Certain other methods can be used to detect binding of anti-CD79b antibodies to CD79b. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, labeled anti-CD79b antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-CD79b antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulations herein may also contain more than one active compound as necessary for the particular indication being treated, preferably those with complementary activities that do not adversely affect each other. For example, in addition to an anti-CD79b antibody, it may be desirable to include in the one formulation, an additional antibody, e.g., a second anti-CD79b antibody which binds a different epitope on the CD79b polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-CD79b antibodies (e.g., anti-CD79b/CD3 TDB antibody) provided herein may be used in therapeutic methods.

In one aspect, an anti-CD79b antibody (e.g., anti-CD79b/CD3 TDB antibody) for use as a medicament is provided. In further aspects, an anti-CD79b antibody (e.g., anti-CD79b/CD3 TDB antibody) for use in treating or delaying progression of a cell proliferative disorder (e.g., cancer and/or B cell proliferative disease) is provided. In certain embodiments, an anti-CD79b antibody (e.g., anti-CD79b/anti-CD3 bispecific antibody) for use in a method of treatment is provided. In certain embodiments, the invention provides an anti-CD79b antibody (e.g., anti-CD79b/CD3 TDB antibody) for use in a method of treating an individual having a cell proliferative disorder comprising administering to the individual an effective amount of the anti-CD79b antibody (e.g., anti-CD79b/CD3 TDB antibody). In one such embodiment, the method further comprises administering to the individual an effective amount of at least one additional therapeutic agent, for example, as described below. In further embodiments, the invention provides an anti-CD79b antibody (e.g., anti-CD79b/CD3 TDB antibody) for use in enhancing immune function in an individual having a cell proliferative disorder. In certain embodiments, the invention provides an anti-CD79b antibody (e.g., anti-CD79b/CD3 TDB antibody) for use in a method of enhancing immune function in an individual having a cell proliferative disorder comprising administering to the individual an effective of the anti-CD79b antibody (e.g., anti-CD79b/CD3 TDB antibody) to activate effector cells (e.g., T cells, e.g., CD8+ and/or CD4+ T cells), expand (increase) an effector cell population, and/or kill a target cell (e.g., target B cell). An "individual" according to any of the above embodiments may be a human.

In a further aspect, the invention provides for the use of an anti-CD79b antibody (e.g., anti-CD79b/CD3 TDB antibody)) in the manufacture or preparation of a medicament.

In one embodiment, the medicament is for treatment of a cell proliferative disorder (e.g., cancer and/or B cell proliferative disorder). In a further embodiment, the medicament is for use in a method of treating a cell proliferative disorder comprising administering to an individual having a cell proliferative disorder an effective amount of the medicament. In one such embodiment, the method further comprises administering to the individual an effective amount of at least one additional therapeutic agent, for example, as described below. In a further embodiment, the medicament is for activating effector cells (e.g., T cells, e.g., CD8+ and/or CD4+ T cells), expanding (increasing) an effector cell population, and/or killing target cells (e.g., target B cells) in the individual. In a further embodiment, the medicament is for use in a method of enhancing immune function in an individual having a cell proliferative disorder or an autoimmune disorder comprising administering to the individual an amount effective of the medicament to activate effector cells (e.g., T cells, e.g., CD8+ and/or CD4+ T cells), expand (increase) an effector cell population, and/or kill a target cell (e.g., target B cell). An "individual" according to any of the above embodiments may be a human.

In a further aspect, the invention provides a method for treating a cell proliferative disorder (e.g., cancer and/or B cell proliferative disorder). In one embodiment, the method comprises administering to an individual having such a cell proliferative disorder an effective amount of an anti-CD79b antibody (e.g., anti-CD79b/CD3 TDB antibody). In one such embodiment, the method further comprises administering to the individual an effective amount of at least one additional therapeutic agent, for example, as described below. An "individual" according to any of the above embodiments may be a human.

In a further aspect, the invention provides a method for enhancing immune function in an individual having a cell proliferative disorder in an individual having a cell proliferative disorder. In one embodiment, the method comprises administering to the individual an effective amount of an anti-CD79b antibody (e.g., anti-CD79b/CD3 TDB antibody) to activate effector cells (e.g., T cells, e.g., CD8+ and/or CD4+ T cells), expand (increase) an effector cell population, and/or kill a target cell (e.g., target B cell). In one embodiment, an "individual" is a human.

An anti-CD79b antibody (e.g., anti-CD79b/CD3 TDB antibody) of the invention may be used in, for example, in vitro, ex vivo, and in vivo therapeutic methods. In one aspect, the invention provides methods for inhibiting cell growth or proliferation, either in vivo or in vitro, the method comprising exposing a cell to an anti-CD79b antibody thereof under conditions permissive for binding to CD79b. "Inhibiting cell growth or proliferation" means decreasing a cell's growth or proliferation by at least 10%, 20%, 30%, 40%, 50%, 60%, 70%, 80%, 90%, 95%, or 100%, and includes inducing cell death. In certain embodiments, the cell is a tumor cell. In certain embodiments, the cell is a B cell. In certain embodiments, the cell is a xenograft, e.g., as exemplified herein.

In one aspect, an anti-CD79b antibody (e.g., anti-CD79b/CD3 TDB antibody) of the invention is used to treat or prevent a B cell proliferative disorder. In certain embodiments, the cell proliferative disorder is associated with increased expression and/or activity of CD79b. For example, in certain embodiments, the B cell proliferative disorder is associated with increased expression of CD79b on the surface of a B cell. In certain embodiments, the B cell proliferative disorder is a tumor or a cancer. Examples of B cell proliferative disorders to be treated by the antibodies of the invention include, but are not limited to, lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma. In some embodiments of any of the B cell proliferative disorders, the B cell proliferative disorder is resistant to treatment with an anti-CD79b immunoconjugate (e.g., anti-CD79b MMAE immunoconjugate).

In a further aspect, the invention provides pharmaceutical formulations comprising any of the anti-CD79b antibodies (e.g., anti-CD79b/CD3 TDB antibody) provided herein, e.g., for use in any of the above therapeutic methods. In one embodiment, a pharmaceutical formulation comprises any of the anti-CD79b antibodies provided herein and a pharmaceutically acceptable carrier. In another embodiment, a pharmaceutical formulation comprises any of the anti-CD79b antibodies (e.g., anti-CD79b/CD3 TDB antibody) provided herein and at least one additional therapeutic agent, e.g., as described below.

In one embodiment, B-cell proliferative disease includes, but is not limited to, lymphomas (e.g., B-Cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma), c) marginal zone lymphomas (including extranodal marginal zone B-cell lymphoma (Mucosa-associated lymphatic tissue lymphomas, MALT), nodal marginal zone B-cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma), f) hairy cell leukemia, g) lymphocytic lymphoma, Waldenstrom's macroglobulinemia, h) acute lymphocytic leukemia (ALL), chronic lymphocytic leukemia (CLL)/small lymphocytic lymphoma (SLL), B-cell prolymphocytic leukemia, i) plasma cell neoplasms, plasma cell myeloma, multiple myeloma, plasmacytoma, and/or j) Hodgkin's disease.

In some embodiments of any of the methods, the B-cell proliferative disorder is cancer. In some embodiments, the B-cell proliferative disorder is lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), or mantle cell lymphoma. In some embodiments, the B-cell proliferative disorder is NHL, such as indolent NHL and/or aggressive NHL. In some embodiments, the B-cell proliferative disorder is indolent follicular lymphoma or diffuse large B-cell lymphoma. In some embodiments of any of the B cell proliferative disorders, the B cell proliferative disorder is resistant to treatment with an anti-CD79b immunoconjugate (e.g., anti-CD79b MMAE immunoconjugate).

Antibodies of the invention can be used either alone or in combination with other agents in a therapy. For instance, an antibody of the invention may be co-administered with at least one additional therapeutic agent and/or adjuvant. In certain embodiments, an additional therapeutic agent is a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubincin, vincristine (Oncovin™) prednisolone, CHOP, CHP, CVP, or COP, or immunotherapeutics such as anti-CD20 (e.g., Rituxan®) or anti-VEGF (e.g., Avastin®), wherein the combination therapy is useful in the treatment of cancers and/or B cell disorders such as B cell proliferative disorders including lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma. In other embodiments, for instance, an antibody of the invention may be co-administered with at least one additional therapeutic agent. In certain embodiments, an additional therapeutic agent is a chemotherapeutic agent, growth inhibitory agent, cytotoxic agent, agent used in radiation therapy, anti-angiogenesis agent, apoptotic agent, anti-tubulin agent, or other agent, such as a epidermal growth factor receptor (EGFR) antagonist (e.g., a tyrosine kinase inhibitor), HER1/EGFR inhibitor (e.g., erlotinib (Tarceva™), platelet derived growth factor inhibitor (e.g., Gleevec™ (Imatinib Mesylate)), a COX-2 inhibitor (e.g., celecoxib), interferon, cytokine, antibody other than the anti-CD3 antibody of the invention, such as an antibody that bind to one or more of the following targets ErbB2, ErbB3, ErbB4, PDGFR-beta, BlyS, APRIL, BCMA VEGF, or VEGF receptor(s), TRAIL/Apo2, or another bioactive or organic chemical agent.

In some embodiments, the methods may further comprise an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy may be a separate administration of one or more of the therapeutic agents described above.

In some embodiments of any of the methods, the additional therapeutic agent is a glucocorticoid. In some embodiments, the glucocorticoid is selected from the group consisting of dexamethasone, hydrocortisone, cortisone, prednisolone, prednisone, methylprednisone, triamcinolone, paramethasone, betamethasone, fludrocortisone, and pharmaceutically acceptable esters, salts, and complexes thereof. In some embodiments, the glucocorticoid is dexamethasone. In some embodiments, the glucocorticoid is a pharmaceutically acceptable ester, salt, or complex of dexamethasone. In some embodiments, the glucocorticoid is dexamethasone.

In some embodiments of any of the methods, the additional therapy comprises an anti-CD20 antibody. In some embodiments, the anti-CD20 antibody is rituximab. In some embodiments, the anti-CD20 antibody is a humanized B-Ly1 antibody. In some embodiments, the humanized B-Ly1 antibody is obinituzumab. In some embodiments, the anti-CD20 antibody is ofatumumab, ublituximab, and/or ibritumomab tiuxetan.

In some embodiments of any of the methods, the additional therapy comprises an alkylating agent. In some embodiments, the alkylating agent is 4-[5-[Bis(2-chloroethyl)amino]-1-methylbenzimidazol-2-yl]butanoic acid and salts thereof. In some embodiments, the alkylating agent is bendamustine.

In some embodiments of any of the methods, the additional therapy comprises a BCL-2 inhibitor. In some embodiments, the BCL-2 inhibitor is 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide and salts thereof. In some embodiments, the BCL-2 inhibitor is venetoclax (CAS #: 1257044-40-8).

In some embodiments of any of the methods, the additional therapy comprises a phosphoinositide 3-kinase (PI3K) inhibitor. In some embodiments, the PI3K inhibitor inhibits delta isoform PI3K (i.e., P110δ). In some embodiments, the PI3K inhibitor is 5-Fluoro-3-phenyl-2-[(1S)-1-(7H-purin-6-ylamino)propyl]-4(3H)-quinazolinone and salts thereof. In some embodiments, the PI3K inhibitor is idelalisib (CAS #: 870281-82-6). In some embodiments, the PI3K inhibitor inhibits alpha and delta isoforms of PI3K. In some embodiments, the PI3K inhibitor is 2-{3-[2-(1-Isopropyl-3-methyl-1H-1,2-4-triazol-5-yl)-5,6-dihydrobenzo[f]imidazo[1,2-d][1,4]oxazepin-9-yl]-1H-pyrazol-1-yl}-2-methylpropanamide and salts thereof.

In some embodiments of any of the methods, the additional therapy comprises a Bruton's tyrosine kinase (BTK) inhibitor. In some embodiments, the BTK inhibitor is 1-[(3R)-3-[4-Amino-3-(4-phenoxyphenyl)-1H-pyrazolo[3,4-d]pyrimidin-1-yl]piperidin-1-yl]prop-2-en-1-one and salts thereof. In some embodiments, the BTK inhibitor is ibrutinib (CAS #: 936563-96-1).

In some embodiments of any of the methods, the additional therapy comprises thalidomide or a derivative thereof. In some embodiments, the thalidomide or a derivative thereof is (RS)-3-(4-Amino-1-oxo 1,3-dihydro-2H-isoindol-2-yl)piperidine-2,6-dione and salts thereof. In some embodiments, the thalidomide or a derivative thereof is lendalidomide (CAS #: 191732-72-6).

In some embodiments of any of the methods, the additional therapy comprises one or more of cyclophosphamide, doxorubicin, vincristine, or prednisolone (CHOP). In some embodiments, the additional therapy further comprises an anti-CD20 antibody as described above (e.g., GA-101 and/or Rituxan).

In some embodiments of any of the methods, the additional therapy comprises one or more of cyclophosphamide, doxorubicin, or prednisolone (CHP). In some embodiments, the additional therapy further comprises an anti-CD20 antibody as described above (e.g., GA-101 and/or Rituxan). In some embodiments, the additional therapy further comprises an anti-CD79b antibody drug conjugate. In some embodiments, the anti-CD79b antibody drug conjugate is anti-CD79b-MC-vc-PAB-MMAE. In some embodiments, the anti-CD79b antibody drug conjugate is described in any one of U.S. Pat. No. 8,088,378 and/or US 2014/0030280, which are hereby incorporated by reference in their entirety. In some embodiments, the anti-CD79b antibody drug conjugate is polatuzumab vedotin. In some embodiments of any of the B cell proliferative disorders, the B cell proliferative disorder is resistant to treatment with an anti-CD79b antibody drug conjugate (e.g., anti-CD79b MMAE antibody drug conjugate). In some embodiments, the anti-CD79b antibody drug conjugate is polatuzumab vedotin.

In some embodiments of any of the methods, the additional therapy comprises a PD-1 axis binding antagonist. In some embodiments of any of the methods, the additional therapy comprises a PD-1 binding antagonist. In some embodiments of any of the methods, the additional therapy comprises a PD-L1 binding antagonist. In some embodiments of any of the methods, the additional therapy comprises a PD-L2 binding antagonist.

In some embodiments of any of the methods, an antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein. In some embodiments, the administration is subcutaneous.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

As a general proposition, the therapeutically effective amount of the anti-CD79b antibody (e.g., anti-CD79b/CD3 TDB antibody) administered to human will be in the range of about 0.01 to about 100 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In one embodiment, an anti-CD79b antibody (e.g., anti-CD79b/CD3 TDB antibody) described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, for example, every week or every three weeks (e.g., such that the patient receives from about two to about twenty, or, for example, about six doses of the anti-CD79b antibody (e.g., anti-CD79b/CD3 TDB antibody). An initial higher loading dose, followed by one or more lower doses may be administered. The progress of this therapy is easily monitored by conventional techniques and assays.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-CD79b antibody.

III. Examples

The following are examples of methods and compositions of the invention. It is understood that various other embodiments may be practiced, given the general description provided above.

Example 1

Materials and Methods

A. Monoclonal Antibody Generation

Protein for immunization of mice was generated by transient transfection of vectors that express Fc-tagged or His-tagged extra-cellular domain (ECD) of human CD79b into CHO cells. The proteins were purified from the transfected cell supernatants on protein A columns and the identity of the protein confirmed by N-terminal sequencing. Ten Balb/c mice (Charles River Laboratories, Hollister, Calif.) were hyperimmunized with recombinant Fc-tagged or His-tagged ECD of human CD79b. B cells from mice demonstrating high antibody titers against the human CD79b immunogen by direct ELISA, and specific binding to Ramos cells, were fused with mouse myeloma cells (X63.Ag8.653; American Type Culture Collection, Rockville, Md.) as previously described (Hongo, J. S. et al., *Hybridoma*, 14:253-260 (1995); Kohler, G. et al., *Nature*, 256:495-497 (1975); Freund, Y. R. et al., *J. Immunol.*, 129:2826-2830 (1982)). After 10 to 12 days, the supernatants were harvested and screened for antibody production and binding by direct ELISA and FACS as indicated above. Positive clones, showing the highest immunobinding after the second round of subcloning by limiting dilution, were expanded and cultured for further characterization, including human CD79b specificity and cross-reactivity. The supernatants harvested from each hybridoma lineage were purified by affinity chromatography (Pharmacia fast protein liquid chromatography (FPLC); Pharmacia, Uppsala, Sweden) as previously described (Hongo, J. S. et al., *Hybridoma*, 14:253-260 (1995); Kohler, G. et al., *Nature*, 256:495-497 (1975); Freund, Y. R. et al., *J. Immunol.*, 129:2826-2830 (1982)). The purified antibody preparations were then sterile filtered (0.2-Φm pore size; Nalgene, Rochester N.Y.) and stored at 4° C. in phosphate buffered saline (PBS).

B. Generation of TDBs

TDB antibodies were produced as full-length antibodies in the knob-into-hole format as human IgG1, as previously described (Atwell et al. *J. Mol. Biol.* 270: 26-35, 1997). Half antibodies were expressed in either *E. coli* or Chinese hamster ovary (CHO) cells, purified by Protein A-affinity chromatography, and the proper half antibody pairs were annealed in vitro as described previously (Spiess et al. *Nat. Biotechnol.* 2013). If TDB antibody production was carried out in CHO cells, the antibody may include an aglycosylation mutation, for example, at residue N297 (e.g., N297G), such that the TDB antibody was an effector-less variant and unable to initiate antibody-dependent cell-mediated cytotoxicity (ADCC).

After annealing, the anti-CD79b/CD3 TDB antibodies were purified by Hydrophobic Interaction Chromatography (HIC) and characterized by analytical gel filtration, mass spectrometry, and polyacrylamide gel electrophoresis. The purified antibodies ran as a single peak (>99% of the signal) in gel filtration with less than 0.2% aggregates. No homodimers were detected by mass spectrometry.

C. Binding Affinity

Binding affinities for the each of the CD3/CD79b TDBs were tested by Biacore or FACS analysis. Briefly, for Biacore binding assays, human CD3γε was immobilized on Biacore Series S CM5 sensor chip using the amine coupling kit from Biacore and anti-CD79b/CD3 TDB antibodies or Fab variants thereof were in the flow through. For FACS binding assays, BJAB cells (for B cell antigens) or other cell lines as specified were incubated with various concentrations of TDB antibodies at 4° C. for 30 minutes, then cells were washed and incubated with 2$^{nd}$ antibody (anti-huIgG-PE; BD Bioscience) for another 15 minutes, before cells were washed again and ready for FACS analysis.

D. In Vitro B Cell Killing and T Cell Activation Assays

The generated anti-CD79b/CD3 TDB antibodies were tested for their ability to support B cell killing and the activation of cytotoxic T cells. In these assays, PBMCs were isolated from whole blood of healthy donors by Ficoll separation. Briefly, human blood was collected in heparinized syringes, and PBMC were isolated using Leucosep (Greiner Bio-one, cat #227290P) and Ficoll Paque Plus (GE Healthcare Biosciences, cat #95038-168), as recommended by the manufacture. If needed CD4+T and CD8+ T cells were separated with Miltenyi kits according to manufacturer's instructions.

Cells were washed in RPMI medium containing 10% FBS, supplemented with GlutaMax (Gibco, cat #35050-061), penicillin & streptomycin (Gibco, cat #15140-122), and ~0.2 million suspended cells were added to a 96-well U-bottom plate. Cells were cultured in RPMI1640 supplemented with 10% FBS (Sigma-Aldrich) at 37° C. in a humidified standard cell culture incubator. For BJAB cell killing assays, 20,000 BJAB cells were incubated with effector cells either as huPBMCs or purified T cells as indicated ratios per assay, in the presence of various concentrations of TDB antibodies for 24 hours, unless otherwise specified. For endogenous B cell killing assays, 200,000 huPBMCs were incubated with various concentrations of anti-CD79b/CD3 TDB antibodies for 24 hours, unless otherwise specified.

After culturing, cells were washed with FACS buffer (0.5% BSA, 0.05% Na Azide in PBS). Cells were then stained in FACS buffer, washed with FACS buffer and suspend in 100 ul of FACS buffer containing 1 ug/ml Propidium Iodide. Data was collected on a FACSCalibur flow cytometer and analyzed using FlowJo. Live B cells were gated out as PI-CD19+ or PI-CD20+ B cells by FACS, and absolute cell count was obtained with FITC beads added to reaction mix as internal counting control. % of cell killing was calculated based on non-TDB treated controls. Activated T cells were detected by CD69 and CD25 surface expression using anti-CD69-FITC (BD, cat #555530) and anti-CD25-PE (BD, cat #555432).

D. In Vivo Efficacy

50 SCID.bg mice were inoculated with 5 million BJAB-luc anti-CD79b-MC-vc-PAB-MMAE resistant model T1.1 X1 cells in HBSS subcutaneously in a volume of 0.2 mL per mouse in the right unilateral-thoracic (not to exceed 200 ul) or a mixture of 5 million BJAB-luc anti-CD79b-MC-vc-PAB-MMAE resistant model T1.1 X1 cells and 10 million PBMCs in HBSS a volume of 0.2 ml (not to exceed 200 ul). This was a preventative study so inoculation and treatment were administered on Day 0.

There were five study groups: 1) 5 million BJAB-luc anti-CD79b-MC-vc-PAB-MMAE resistant model T1.1 X1, Vehicle, qwx2, IV; 2) 5 million BJAB-luc anti-CD79b-MC-vc-PAB-MMAE resistant model T1.1 X1, 0.5 mg/kg anti-CD79 TDB, qwx2, IV; 3) 5 million BJAB-luc anti-CD79b-MC-vc-PAB-MMAE resistant model T1.1 X1+10×10^6 PBMCs (pre-mixed), Vehicle, qwx2, IV; 4) 5 million BJAB-luc anti-CD79b-MC-vc-PAB-MMAE resistant model T1.1 X1+10×10^6 PBMCs (pre-mixed), 0.5 mg/kg anti-CD79 TDB (CD79b.A7.v14b/38E4v1), qwx2, IV; and 5) 5 BJAB-luc anti-CD79b-MC-vc-PAB-MMAE resistant model T1.1 X1, 8 mg/kg BJAB-luc anti-CD79b-MC-vc-PAB-MMAE, once, IV. PBMCs were from Buffy Coat Donor, cultured overnight in non-activating condition, inoculated as a mixture with the BJAB cells. All treatments were administered i.v., tail vein, volume=0.1 ml (not to exceed 200 ul). Tumors were measured 1-2 times per week. Body weights were measured 1-2×/week up to 14 days after the final treatment.

1. Selection of CD79b TDB-Anti-CD79b Antigen Arm

Antibody—drug conjugates (ADC) have been generated (such as the humanized anti-CD79b antibody (humanized SN8) conjugated to monomethylauristatin E (MMAE) by a protease cleavable linker), which has shown in the clinic to be efficacious for the treatment of NHL. See U.S. Pat. No. 8,088,378 and Morschhauser et al., "4457 *Updated Results of a Phase II Randomized Study (ROMULUS) of Polatuzumab Vedotin or Pinatuzumab Vedotin Plus Rituximab in Patients with Relapsed/Refractory Non-Hodgkin Lymphoma*" 56$^{th}$ ASH Annual Meeting and Exposition: Dec. 6-9, 2014.

Based on the clinical success of the anti-CD79b ADC, the humanized SN8 antibody was in a T-cell dependent bispecific (TDB) antibody format to harness the high cytotoxic potential of T cells in eradicating tumor cells. See U.S. Pat. No. 8,088,378, which is hereby incorporated by reference in its entirety. An anti-CD3 (e.g., UCHT1.v9; see, e.g., Zhu et al. *Int. J. Cancer* 62:319-324 (1995))/anti-CD79b (e.g., SN8.v28) bispecific knob & hole (K&H) was generated as described above. However, in endogenous B cell killing assaying using two different donors as described above, poor B cell killing activity for the UCHT1.v9/SN8.v28 bispecific K&H was observed: the EC$_{50}$ was 357 ng/mL and 120 ng/mL the cell killing assay.

A second anti-CD3 (e.g., UCHT1.v9)/anti-CD79b TDB was generated using 2F2 as the anti-CD79b antibody arm. 2F2 had shown in vitro promise as an anti-CD79b ADC. See e.g., US20090068202, incorporated by reference in its entirety. In addition, the CD79b arm antibody SN8.v28 was modified in an attempt to improve cell killing (SN8.new (VH SEQ ID NO:37 and VL SEQ ID NO:38)). As shown in FIG. 1A (endogenous B cell killing assay) and FIG. 1B (BJAB cell killing assay), SN8.v28/UCHT1.v9 bispecific K&H antibodies, SN8.new/UCHT1.v9 bispecific K&H antibodies, as well as 2F2/UCHT1.v9 bispecific K&H antibodies resulted in poor B cell killing activity.

Monoclonal anti-CD79b antibodies were generated as described above. Two of these anti-CD79b antibodies (CD79b.F6 and CD79b.A7) were also tested as bispecific bisfab format anti-CD79b/CD3 antibodies. As shown in FIG. 1C, in an endogenous B cell killing assay, CD79b.F6/UCHT1.v9 bispecific bisfab displayed improved B cell killing compared to SN8.v28/UCHT1.v9 bispecific K&H (EC$_{50}$ of 33 ng/mL compared to 189 ng/mL). Further, as shown in FIG. 1C, in the endogenous B cell killing assay, the bispecific bisfab CD79b.A7/UHT1.v9 dramatically improved B cell killing compared to either bispecific bisfab CD79b.F6/UCHT1.v9 or SN8.v28/UCHT1.v9 bispecific K&H (EC$_{50}$ 12 ng/mL compared to 33 ng/mL and 189 ng/mL). The bispecific bisfab CD79b.A7/UHT1.v9 was further tested for endogenous B cell killing and CD8+ T cell activation using additional donors. As shown in FIGS. 2A and C, in the endogenous B cell killing assay as described above, the bispecific bisfab CD79b.A7/UHT1.v9 using two different donors resulted in efficient B cell killing with an EC$_{50}$ of 7.0 ng/mL and 18 ng/mL, respectively. At the same time, as shown in FIGS. 2B and D in the CD8+ T cell activation assay as described above, the bispecific bisfab CD79b.A7/UHT1.v9 resulted in efficient activation of T cells as evidenced by % of CD69+CD25+ T cells in CD8+ T cells with an EC$_{50}$ of 17 ng/mL and 17 ng/mL, respectively.

In order to better understand the difference in the B cell killing and T cell activation of the different anti-CD79b antigen arms in the anti-CD79b/CD3 TDB antibodies, the properties of the different anti-CD79b antigen arms were analyzed. Binding of CD79b.A7 to BJAB cells in a FACS assay were competed by a 21-amino acid peptide ARSE-DRYRNPKGSACSRIWQS (SEQ ID NO:63) that corresponds to the $NH_2$ termini of huCD79b, but not the 21-amino acid peptide AKSEDLYPNPKGSACSRIWQS (SEQ ID NO:64) that correspond to the $NH_2$ termini of cynoCD79b (data not shown). This is similar to the results of 2F2 and SN8 as described in Zheng et al. *Mol. Cancer Ther.* 8(10):2937-2947 (2009). Therefore, the epitope on CD79b does not appear to account for the difference in B cell killing and T cell activation between SN8.v28/UCHT1.v9, 2F2/UCHT1.v9, and CD79.A7.

The monovalent and bivalent anti-CD79b antibody binding affinity was also evaluated in order to better understand the contribution, if any, to B cell killing activity. Binding affinity of dual arm, bivalent anti-CD79b antibodies and bispecific anti-CD79b/CD3 antibodies using BJAB cells were also analyzed. Initial experiments indicated that the binding affinity by $EC_{50}$ on BJAB cell of the dual arm, bivalent anti-CD79b antibody SN8.v28 was 0.04 μg/mL, while the binding affinity of by $EC_{50}$ on BJAB cell of the anti-CD79b/CD3 bispecific K&H (SN.v28/UCHT1.v9) was only 3.7 μg/mL. Similarly as shown in FIG. 3A, the binding affinity by $EC_{50}$ on BJAB cell of the dual arm, bivalent anti-CD79b antibody 2F2 was significantly higher than the anti-CD79b/CD3 bispecific K&H (SN8.v28/UCHT1.v9, SN8new/UCHT1.v9, and 2F2/UCHT.v9). The binding affinity of the additional anti-CD79 antibodies, CD79b.F6 and CD79b.A7, were tested in the dual arm, bivalent anti-CD79b antibody format as well as the bisfab and K&H bispecific anti-CD79b/CD3 antibodies. As shown in FIG. 3B, the binding affinity of dual arm, bivalent anti-CD79b antibody CD79.A7 by $EC_{50}$ on BJAB cell was 0.3 μg/mL. The binding affinity by $EC_{50}$ on BJAB cell of the bispecific bisfab anti-CD79b/CD3 (CD79b.A7/UCHT1.v9) was lower than the dual arm, bivalent anti-CD79b antibody CD79.A7, but still relatively high 1.4 μg/mL. The binding affinity by $EC_{50}$ on BJAB cell of the dual arm, bivalent anti-CD79b antibody CD79b.F6 and the K&H and bisfab bispecific anti-CD79b/CD3 antibodies (SN8.v28/UCHT1.v9 and CD79b.F6/CHT1.v9, respectively) was significantly lower. Based on this data, the monovalent binding affinity correlated with the extent of endogenous B cell depletion and % B cell killing.

2. Humanization of Anti-CD79b Antigen Arm

Monoclonal antibody CD79b.A7 was humanized as described above. Residue numbers are according to Kabat et al., Sequences of proteins of immunological interest, 5th Ed., Public Health Service, National Institutes of Health, Bethesda, Md. (1991).

Variants constructed during the humanization of CD79b.A7 were assessed in the form of an IgG. The VL and VH domains from murine CD79b.A7 were aligned with the human VL kappa II (VLK2) and human VH subgroup I (VHI) consensus sequences. Hypervariable regions from the murine antibodies were engineered into VLK2 and VHI acceptor frameworks. Specifically, from the muCD79b.A7 domain, positions 24-34 (L1), 50-56 (L2) and 89-97 (L3) were grafted into VLK2 and from the muCD79b.A7 VH domain, positions 26-35 (H1), 50-65 (H2) and 93-102 (H3) were grafted into VHI.

The binding affinity of the antibodies in this section was determined by BIAcore™ T100. Briefly, BIAcore™ research grade CM5 chips were activated with 1-ethyl-3-(3-dimethylaminopropyl) carbodiimide (EDC) and N-hydroxysuccinimide (NHS) reagents according to the supplier's instructions. Human CD79a fused with an Fc domain at the C-terminus was coupled to the chips. To achieve more monovalent binding events, low density of ~12 response units (RU) was immobilized in each flow cell. For measuring the apparent affinity of the antibodies, ~370 RU of the antigen was immobilized. Unreacted coupling groups were blocked with 1M ethanolamine. For kinetics measurements, three-fold serial dilutions of antibody was injected in PBS-T buffer (0.05% surfactant P20 in PBS) at 25° C. with a flow rate of 30 μl/min. 10 mM glycine, pH 1.7 was used as regeneration buffer at 30 ul/min flow rate for 1 minute. Association rates ($k_{on}$) and dissociation rates ($k_{off}$) were calculated using a 1:1 Langmuir binding model (BIAcore™ T100 Evaluation Software version 2.0). The equilibrium dissociation constant (Kd) was calculated as the ratio $k_{off}/k_{on}$.

The humanized CDR graft of CD79b.A7 (CD79b.A7.v1) did not bind to CD79b. Thus additional humanized variants were made to evaluate the contribution of mouse framework vernier positions towards binding. Six additional light chains (VL1: CDRs graft+(Y36L), VL2: CDRs graft+(Y36L+L46C), VL3: CDRs graft+(I2V+Y36L+L46C), VL4: CDRs graft+(Y36L+L46S), VL5: CDRs graft+(I2V+Y36L+L46S), VL6: CDRs graft+(L46S)) and seven additional heavy chains (VH1a: CDRs graft+(A93S), VH1b: CDRs graft+(R71V+A93S), VH1c: CDRs graft+(V67A+I69L+R71V+A93S), VH1d:CDRs graft+(V67A+I69L+R71V+T73K+A93S), VH1e: CDRs graft+(V67A+R71V+A93S), VH1f: CDRs graft+(I69L+R71V+A93S), and VH1g: CDRs graft+(V67A+I69L)) were constructed and combined to generate the variants in Table 2. Based on the affinities of these variants, Y36L and L46C in the light chain appear to be key mouse vernier residues. Surprisingly, when position 46 was changed to a serine in order to avoid the use of a free cysteine, the affinity of variants with this change improved dramatically. In the heavy chain, V67A, I69L, R71V and A93S also contributed to CD79b binding; however R71V appeared to be the key mouse vernier residues based on this mutational analysis. The affinities in Table 2 are all apparent affinities based on bivalent IgG binding to CD79b immobilized at a low density to approximate monovalent binding. See Table 2 below.

TABLE 2

| CD79b.A7 nM | K2 graft | VL1 | VL2 | VL3 | VL4 | VL5 | VL6 |
|---|---|---|---|---|---|---|---|
| VH1 graft | v1 No Binding | v2 NDB | v3 320 nM | | | | |
| VH1a | v4 NDB | v5 NDB | v6 3800 nM | | | | |
| VH1b | v7 NDB | v8 NDB | v9 7050 nM | | v27 8 nM | | |
| VH1c | v10 NDB | v11 NDB | v12 20 nM | v13 716 nM | v14 5 nM | v15 5 nM | v26 23 nM |
| VH1d | | | v16 117 nM | v17 88 nM | v18 4 nM | v19 4 nM | |
| VH1e | | | | | v20 8 nM | | v23 20 nM |
| VH1f | | | | | v21 8 nM | | v24 39 nM |
| VH1g | | | | | v22 16 nM | | v25 68 nM |

Binding affinity was further tested by FACS analysis, BJAB cells were incubated with various anti-CD79b antibodies for 30 minutes on ice. At the end of the incubation, cells were washed with ice cold FACS buffer (1×PBS, 2% BSA, 2 mM EDTA), followed by incubation with PE-labeled mouse anti-human IgG antibody (BD bioscience #555787). Flow cytometry analysis was done on a BD LSR analyzer. Bivalent binding was expressed as Mean Fluorescence Intensity (MFI) of PE fluorophore. The binding of chCD79b.A7, huCD79b.A7.v12 and huCD79b.A7.v14 to BJAB-luciferase cells was at an $EC_{50}$ of 124 ng/mL, 400 ng/mL, and 68 ng/mL, respectively.

Binding affinity of the humanized CD79.A7.v14 of monovalent and bivalent was tested as described above. As shown in FIG. 3C, the monovalent CD79.A7.v14 (in the K&H TDB format CD79.A7.v14/40G5c) had an $EC_{50}$ of 220 ng/ml while the bivalent, dual arm CD79A7.v14 had an $EC_{50}$ of 46.8 ng/ml.

The humanized antibody CD79.A7.v14 was tested under thermal stress (40° C., pH 5.5, 2 weeks) and 2,2'-azobis (2-amidinopropane) hydrochloride (AAPH) Analysis. Samples were thermally stressed to mimic stability over the shelf life of the product. Samples were buffer exchanged into 20 mM His Acetate, 240 mM sucrose, pH 5.5 and diluted to a concentration of 1 mg/mL. One mL of sample was stressed at 40 C for 2 weeks and a second was stored at −70 C as a control. Both samples were then digested using trypsin to create peptides that could be analyzed using liquid chromatography (LC)-mass spectrometry(MS) analysis. For each peptide in the sample retention time, from the LC as well as high resolution accurate mass and peptide ion fragmentation information (amino acid sequence information) were acquired in the MS. Extracted ion chromatograms (XIC) were taken for peptides of interest (native and modified peptide ions) from the data sets at a window of +−10 ppm and peaks were integrated to determine area. Relative percentages of modification were calculated for each sample by taking the (area of the modified peptide) divided by (area of the modified peptide plus the area of the native peptide) multiplied by 100.

W33 in CDR-H1 and M62 in CDR-H2 of CD79b.A7.v14 were shown to be susceptible to oxidation (W33 oxidation increased by 73.7% and M62 oxidation increased by 64.8%). Variants of CD79b.A7.v14 antibodies were tested to determine if potential oxidation could be reduced without affecting binding to huCD79b. The variant, CD79b.A7.v14b, eliminated these potential oxidation problems by changing these regions to match the human VH1 consensus (W33Y, M62K, K64Q and D65G). These changes did not alter the affinity for CD79b binding. See data not shown.

3. Selection of CD79b TDB-Anti-CD3 Antigen Arm

The effect of the CD3 binding domain pairing on efficiency of anti-CD79b TDB antibody B cell killing was analyzed. The anti-CD79b.A7.v14 antibody was tested in combination with different anti-CD3 antibody binding domains including 40G5c and 38E4v1. 200,000 PBMCs were incubated with or without anti-CD79b/CD3 TDB antibody for 48 hours. The percent of B cell killing in FIG. 5A was calculated as follows: (live B cell number without TDB—live B cell number with TDB)/(live B cell number without TDB)*100. T cell activation as shown in FIG. 5B was measured by gating on $CD69^+/CD25^+$ cells in $CD8^+$ T cell population. As shown in FIGS. 5A and B, K&H CD79b.A7.v14/40G5c showed poor CD8+T activation and low percentage of endogenous B cell killing. In additional experiments (data not shown), the anti-CD79b/CD3 TDB antibody (CD79b.A7.v14/40G5c K&H) showed an $EC_{50}$ of 1.1 and 2.3 ng/mL for CD8+T activation and an $EC_{50}$ of 2658 and 288 ng/mL for endogenous B cell killing using two different donors. In contrast, as shown in FIGS. 5A and B, the anti-CD79b/CD3 TDB antibody (CD79b.A7.v14/38E4v1 K&H) showed substantially improved CD8+ T cell activation and percentage of endogenous B cell killing—an $EC_{50}$ of 15 ng/mL for endogenous B cell killing compared to CD79b.A7.v14/40G5c K&H. In additional experiments (data not shown), the anti-CD79b/CD3 TDB antibody (CD79b.A7.v14/40G5c K&H) showed an $EC_{50}$ of 401, 14, 1.5, 10, 12, and 16 ng/mL for endogenous B cell killing using six different donors.

B cell killing and T cell activation activity of the anti-CD79b/CD3 TDB antibody (CD79b.A7.v14/40G5c K&H) were also tested in BJAB and WSU-DLCL2 cell lines as described above and in the FIG. 6 Figure Legend. As shown in FIGS. 6A and B, the anti-CD79b/CD3 TDB antibody (CD79b.A7.v14/40G5c K&H) showed significant CD8+T activation and percentage of B cell killing—an $EC_{50}$ of 85 ng/mL for BJAB B cell killing and 82 ng/mL for WSU-DLCL2 B cell killing. The $EC_{50}$ for CD8+ T cell activation with BJAB and WSU-DLCL2 B cells was 18 and 39 ng/mL, respectively.

B cell killing activity of the anti-CD79b/CD3 TDB antibody (CD79b.A7.v14b/40G5c K&H) was tested in various cell lines as described in FIG. 7A-B. The HT cell line is a non-CD79b expressing cell. The percent of B cell killing was calculated as follows: (live B cell number without TDB—live B cell number with TDB)/(live B cell number without TDB)*100. As shown in FIG. 7A, in a dose response curve of B cell killing for BJAB, WSU-DLCL2, and OCI-LY-19 cells, the $EC_{50}$ of 8.87, 2.63, and 17.41 ng/mL for OCI-Ly-19, BJAB, and WSU-DLCL2 B cell killing, respectively. FIG. 7B shows significant B cell killing with 5000 ng/ml anti-CD79/CD3 TDB antibody (CD79b.A7.v14b/38E4v1 K&H) across multiple cell lines (duplicate, average±STD).

The varied efficacies of the generated TDB antibodies with bispecific for CD3 and CD79b, underscore the critical and unpredictable contributions of both antibody arms in the generation of an exemplary TDB possessing high efficacy 4. In Vitro and In Vivo Efficacy in Anti-CD79b-MC-Vc-PAB-MMAE Resistant B Cells The B cell killing activity of anti-CD79b/CD3 TDB antibodies (CD79b.A7.v14b/38E4v1) in vitro and in vivo were also tested in anti-CD79b-MC-vc-PAB-MMAE Resistant B cells. BJAB cell variants (BJAB-CD79b ADC-R T1.1 and BJAB-SN8v28vcE CD79b ADC-R T1.2) were derived from non-responsive BJAB xenograft tumors in anti-CD79b-MC-vc-PAB-MMAE Resistant B cells treated mice. As shown in FIG. 8A, the anti-CD79b/CD3 TDB (CD79b.A7.v14b/38E4v1) was very effective in BJAB as well as anti-CD79b-MC-vc-PAB-MMAE Resistant BJAB cells cell killing in vitro. Further, as shown in FIG. 8B, anti-CD79b/CD3 TDB antibody (CD79b.A7.v14b/38E4v1) prevents anti-CD79b-MC-vc-PAB-MMAE Resistant BJAB tumor growth in vivo.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

| NAME | SEQUENCE | SEQ ID NO |
|---|---|---|
| Human CD79b precursor; Acc. No. NP_000617.1; signal sequence = amino acids 1 to 28 | RFIARKRGFT VKMHCYMNSA SGNVSWLWKQ EMDENPQQLK LEKGRMEESQ NESLATLTIQ GIRFEDNGIY FCQQKCNNTS EVYQGCGTEL RVMGFSTLAQ LKQRNTLKDG IIMIQTLLII LFIIVPIFLL LDKDDSKAGM EEDHTYEGLD IDQTATYEDI VTLRTGEVKW SVGEHPGQE | 1 |
| Human mature CD79b, without signal sequence; amino acids 29 to 229 | AR SEDRYRNPKG SACSRIWQSP RFIARKRGFT VKMHCYMNSA SGNVSWLWKQ EMDENPQQLK LEKGRMEESQ NESLATLTIQ GIRFEDNGIY FCQQKCNNTS EVYQGCGTEL RVMGFSTLAQ LKQRNTLKDG IIMIQTLLII LFIIVPIFLL LDKDDSKAGM EEDHTYEGLD IDQTATYEDI VTLRTGEVKW SVGEHPGQE | 2 |
| CD79b.A7, CD79b.A7.v14 CD79b.A7.v15 CD79b.A7.v18 CD79b.A7.v19 CD79b.A7.v20 CD79b.A7.v21 HVR-H1 | TYWMN | 3 |
| CD79b.A7.v14b HVR-H1 | TYYMN | 4 |
| Consensus HVR-H1 | TYX$_1$MN, wherein X$_1$ is W or Y | 5 |
| CD79b.A7, CD79b.A7.v14 CD79b.A7.v15 CD79b.A7.v18 CD79b.A7.v19 CD79b.A7.v20 CD79b.A7.v21 HVR-H2 | MIDPSDSETHYNQMFKD | 6 |
| CD79b.A7.v14b HVR-H2 | MIDPSDSETHYNQKFQG | 7 |
| Consensus HVR-H2 | MIDPSDSETHYNQX$_2$FX$_3$X$_4$, wherein X$_2$ is M or K, X$_3$ is K or Q, and X$_4$ is D or G. | 8 |
| CD79b.A7, CD79b.A7.v14 CD79b.A7.v14b CD79b.A7.v15 CD79b.A7.v18 CD79b.A7.v19 CD79b.A7.v20 CD79b.A7.v21 HVR-H3 | SLAF | 9 |
| CD79b.A7, CD79b.A7.v14 CD79b.A7.v14b CD79b.A7.v15 CD79b.A7.v18 CD79b.A7.v19 CD79b.A7.v20 CD79b.A7.v21 HVR-L1 | KSSQSLLDSDGKTYLN | 10 |
| CD79b.A7, CD79b.A7.v14 CD79b.A7.v14b CD79b.A7.v15 CD79b.A7.v18 CD79b.A7.v19 CD79b.A7.v20 CD79b.A7.v21 HVR-L2 | LVSKLDS | 11 |
| CD79b.A7, CD79b.A7.v14 CD79b.A7.v14b CD79b.A7.v15 CD79b.A7.v18 | WQGTHFPQT | 12 |

| NAME | SEQUENCE | SEQ ID NO |
|---|---|---|
| CD79b.A7.v19 | | |
| CD79b.A7.v20 | | |
| CD79b.A7.v21 | | |
| HVR-L3 | | |
| K2H1 Heavy Chain Variable Region (V$_H$) | EVQLVQSGAEVKKPGASVKVSCKASGYTFTSYYIHWVRQAPGQGLEW IGWINPGSGNTNYAQKFQGRVTITRDTSTSTAYLELSSLRSEDTAVY YYCARFDYWGQGTLVTVSS | 13 |
| K2H1 Light Chain Variable Region(V$_L$) | DIVMTQTPLSLPVTPGQPASISCRSSQSLLHSSGNTYLDWYLQKPGQ SPQLLIYLGSNRASGVPDRFSGSGSGTDFTLKISRVEAEDVGVYYCQ QAIQFPPFTFGQGTKVEIK | 14 |
| CD79b.A7 V$_H$ | QVQLQQPGVELVRPGASVKLSCKASGYTFTTYWMNWVRQRPGQGLDW IGMIDPSDSETHYNQMFKDKATLTVDKSSSTAYIQLNSLTSEDSAVY YCSRSLAFWGQGTLVTVSA | 15 |
| CD79b.A7 V$_L$ | DVVMTQTPLTLSVTIGQPASISCKSSQSLLDSDGKTYLNWLLQRPGQ SPKCLIYLVSKLDSGVPDRFTGSGSGTDFTLKISRVEAEDLGVYYCW QGTHFPQTFGGGTKLEIK | 16 |
| CD79b.A7.v14 V$_H$ | EVQLVQSGAEVKKPGASVKVSCKASGYTFTTYWMNWVRQAPGQGLEW IGMIDPSDSETHYNQMFKDRATLTVDTSTSTAYLELSSLRSEDTAVY YCSRSLAFWGQGTLVTVSS | 17 |
| CD79b.A7.v14 V$_L$ | DIVMTQTPLSLPVTPGQPASISCKSSQSLLDSDGKTYLNWLLQKPGQ SPQSLIYLVSKLDSGVPDRFSGSGSGTDFTLKISRVEAEDVGVYYCW QGTHFPQTFGQGTKVEIK | 18 |
| CD79b.A7.v14b V$_H$ | EVQLVQSGAEVKKPGASVKVSCKASGYTFTTYYMNWVRQAPGQGLEW IGMIDPSDSETHYNQKFQGRATLTVDTSTSTAYLELSSLRSEDTAVY YCSRSLAFWGQGTLVTVSS | 19 |
| CD79b.A7.v14b V$_L$ | DIVMTQTPLSLPVTPGQPASISCKSSQSLLDSDGKTYLNWLLQKPGQ SPQSLIYLVSKLDSGVPDRFSGSGSGTDFTLKISRVEAEDVGVYYCW QGTHFPQTFGQGTKVEIK | 20 |
| CD79b.A7.v15 V$_H$ | EVQLVQSGAEVKKPGASVKVSCKASGYTFTTYWMNWVRQAPGQGLEW IGMIDPSDSETHYNQMFKDRATLTVDTSTSTAYLELSSLRSEDTAVY YCSRSLAFWGQGTLVTVSS | 21 |
| CD79b.A7.v15 V$_L$ | DVVMTQTPLSLPVTPGQPASISCKSSQSLLDSDGKTYLNWLLQKPGQ SPQSLIYLVSKLDSGVPDRFSGSGSGTDFTLKISRVEAEDVGVYYCW QGTHFPQTFGQGTKVEIK | 22 |
| CD79b.A7.v18 V$_H$ | EVQLVQSGAEVKKPGASVKVSCKASGYTFTTYWMNWVRQAPGQGLEW IGMIDPSDSETHYNQMFKDRATLTVDKSTSTAYLELSSLRSEDTAVY YCSRSLAFWGQGTLVTVSS | 23 |
| CD79b.A7.v18 V$_L$ | DIVMTQTPLSLPVTPGQPASISCKSSQSLLDSDGKTYLNWLLQKPGQ SPQSLIYLVSKLDSGVPDRFSGSGSGTDFTLKISRVEAEDVGVYYCW QGTHFPQTFGQGTKVEIK | 24 |
| CD79b.A7.v19 V$_H$ | EVQLVQSGAEVKKPGASVKVSCKASGYTFTTYWMNWVRQAPGQGLEW IGMIDPSDSETHYNQMFKDRATLTVDKSTSTAYLELSSLRSEDTAVY YCSRSLAFWGQGTLVTVSS | 25 |
| CD79b.A7.v19 V$_L$ | DVVMTQTPLSLPVTPGQPASISCKSSQSLLDSDGKTYLNWLLQKPGQ SPQSLIYLVSKLDSGVPDRFSGSGSGTDFTLKISRVEAEDVGVYYCW QGTHFPQTFGQGTKVEIK | 26 |
| CD79b.A7.v20 V$_H$ | EVQLVQSGAEVKKPGASVKVSCKASGYTFTTYWMNWVRQAPGQGLEW IGMIDPSDSETHYNQMFKDRATITVDTSTSTAYLELSSLRSEDTAVY YCSRSLAFWGQGTLVTVSS | 27 |
| CD79b.A7.v20 V$_L$ | DIVMTQTPLSLPVTPGQPASISCKSSQSLLDSDGKTYLNWLLQKPGQ SPQSLIYLVSKLDSGVPDRFSGSGSGTDFTLKISRVEAEDVGVYYCW QGTHFPQTFGQGTKVEIK | 28 |
| CD79b.A7.v21 V$_H$ | EVQLVQSGAEVKKPGASVKVSCKASGYTFTTYWMNWVRQAPGQGLEW IGMIDPSDSETHYNQMFKDRVTLTVDTSTSTAYLELSSLRSEDTAVY YCSRSLAFWGQGTLVTVSS | 29 |

| NAME | SEQUENCE | SEQ ID NO |
|---|---|---|
| CD79b.A7.v21 V$_L$ | DIVMTQTPLSLPVTPGQPASISCKSSQSLLDSDGKTYLNWLLQKPGQ SPQSLIYLVSKLDSGVPDRFSGSGSGTDFTLKISRVEAEDVGVYYCW QGTHFPQTFGQGTKVEIK | 30 |
| SN8.new HVR-H1 | SYWIE | 31 |
| SN8.new HVR-H2 | EILPGGGDTNYNEIFKG | 32 |
| SN8.new HVR-H3 | RVPIRLDY | 33 |
| SN8.new HVR-L1 | KASQSVDYDGDSFLN | 34 |
| SN8.new HVR-L2 | AARKLGR | 35 |
| SN8.new HVR-L3 | QQSNEDPLT | 36 |
| SN8.new V$_H$ | EVQLVESGGGLVQPGGSLRLSCAASGYTFSSYWIEWVRQAPGKGLEW VGEILPGGGDTNYNEIFKGRFTISADTSKNTAYLQMNSLRAEDTAVY YCTRRVPIRLDYWGQGTLVTVSS | 37 |
| SN8.new V$_L$ | DIQMTQSPSSLSASVGDRVTITCKASQSVDYDGDSFLNWYQQKPGKA PKLLIYAARKLGRGVPSRFSGSGSGTDFTLTISSLQPEDFATYYCQQ SNEDPLTFGQGTKVEIK | 38 |
| 40G5c HVR-H1 | NYYIH | 39 |
| 40G5c HVR-H2 | WIYPGDGNTKYNEKFKG | 40 |
| 40G5c HVR-H3 | DSYSNYYFDY | 41 |
| 40G5c HVR-L1 | KSSQSLLNSRTRKNYLA | 42 |
| 40G5c HVR-L2 | WASTRES | 43 |
| 40G5c HVR-L3 | TQSFILRT | 44 |
| 38E4v1 HVR-H1 | SYYIH | 45 |
| 38E4v1 HVR-H2 | WIYPENDNTKYNEKFKD | 46 |
| 38E4v1 HVR-H3 | DGYSRYYFDY | 47 |
| 38E4v1 HVR-L1 | KSSQSLLNSRTRKNYLA | 48 |
| 38E4v1 HVR-L2 | WTSTRKS | 49 |
| 38E4v1 HVR-L3 | KQSFILRT | 50 |
| UCHT1 v9 HVR-H1 | GYTMN | 51 |
| UCHT1 v9 HVR-H2 | LINPYKGVSTYNQKFKD | 52 |
| UCHT1 v9 HVR-H3 | SGYYGDSDWYFDV | 53 |
| UCHT1 v9 HVR-L1 | RASQDIRNYLN | 54 |
| UCHT1 v9 HVR-L2 | YTSRLES | 55 |
| UCHT1 v9 HVR-L3 | QQGNTLPWT | 56 |
| 40G5c V$_H$ | EVQLVQSGAEVKKPGASVKVSCKASGYTFTNYYIHWVRQAPGQGLEW IGWIYPGDGNTKYNEKFKGRATLTADTSTSTAYLELSSLRSEDTAVY YCARDSYSNYYFDYWGQGTLVTVSS | 57 |
| 40G5c V$_L$ | DIVMTQSPDSLAVSLGERATINCKSSQSLLNSRTRKNYLAWYQQKPG QPPKLLIYWASTRESGVPDRFSGSGSGTDFTLTISSLQAEDVAVYYC TQSFILRTFGQGTKVEIK | 58 |
| 38E4v1 V$_H$ | EVQLVQSGAEVKKPGASVKVSCKASGFTFTSYYIHWVRQAPGQGLEW IGWIYPENDNTKYNEKFKDRVTITADTSTSTAYLELSSLRSEDTAVY YCARDGYSRYYFDYWGQGTLVTVSS | 59 |
| 38E4v1 V$_L$ | DIVMTQSPDSLAVSLGERATINCKSSQSLLNSRTRKNYLAWYQQKPG QSPKLLIYWTSTRKSGVPDRFSGSGSGTDFTLTISSLQAEDVAVYYC KQSFILRTFGQGTKVEIK | 60 |

| NAME | SEQUENCE | SEQ ID NO |
|---|---|---|
| UCHT1v9 $V_H$ | EVQLVESGGGLVQPGGSLRLSCAASGYSFTGYTMNWVRQAPGKDLEW VALINPYKGVSTYNQKFKDRFTISVDKSKNTAYLQMNSLRAEDTAVY YCARSGYYGDSDWYFDVWGQGTLVTVSS | 61 |
| UCHT1v9 $V_L$ | DIQMTQSPSSLSASVGDRVTITCRASQDIRNYLNWYQQKPGKAPKLL IYYTSRLESGVPSRFSGSGSGTDYTLTISSLQPEDFATYYCQQGNTL PWTFGQGTKLELK | 62 |
| Peptide 1 | ARSEDRYRNPKGSACSRIWQS | 63 |
| Peptide 2 | AKSEDLYPNPKGSACSRIWQS | 64 |

What is claimed is:

1. A bispecific antibody that binds to CD79b and CD3, wherein the bispecific antibody comprises:
   (a) a CD79b binding domain comprising the following six hypervariable regions (HVRs):
   an HVR-H1 comprising the amino acid sequence of SEQ ID NO: 5,
   an HVR-H2 comprising the amino acid sequence of SEQ ID NO: 8,
   an HVR-H3 comprising the amino acid sequence of SEQ ID NO: 9,
   an HVR-L1 comprising the amino acid sequence of SEQ ID NO: 10,
   an HVR-L2 comprising the amino acid sequence of SEQ ID NO: 11, and
   an HVR-L3 comprising the amino acid sequence of SEQ ID NO, 12;
   and
   (b) a CD3 binding domain.

2. The bispecific antibody of claim 1, wherein CD3 binding domain comprises the following six HVRs:
   an HVR-H1 comprising the amino acid sequence of SEQ ID NO:45,
   an HVR-H2 comprising the amino acid sequence of SEQ ID NO:46,
   an HVR-H3 comprising the amino acid sequence of SEQ ID NO:47,
   an HVR-L1 comprising the amino acid sequence of SEQ ID NO:48,
   an HVR-L2 comprising the amino acid sequence of SEQ ID NO:49, and
   an HVR-L3 comprising the amino acid sequence of SEQ ID NO:50.

3. The bispecific antibody of claim 2, wherein the CD3 binding domain comprises
   (a) a VH sequence having at least 95% sequence identity to the amino acid sequence of SEQ ID NO:59;
   (b) a VL sequence having at least 95% sequence identity to the amino acid sequence of SEQ ID NO:60; or
   (c) a VH sequence as in (a) and a VL sequence as in (b).

4. The bispecific antibody of claim 1, wherein the CD3 binding domain comprises a VH sequence of SEQ ID NO:59 and a VL sequence of SEQ ID NO:60.

5. A bispecific antibody that binds to CD79b and CD3, wherein the bispecific antibody comprises:
   (a) a CD79b binding domain comprising the following six hypervariable regions (HVRs):
   an HVR-H1 comprising the amino acid sequence of SEQ ID NO: 3,
   an HVR-H2 comprising the amino acid sequence of SEQ ID NO: 6,
   an HVR-H3 comprising the amino acid sequence of SEQ ID NO: 9,
   an HVR-L1 comprising the amino acid sequence of SEQ ID NO: 10,
   an HVR-L2 comprising the amino acid sequence of SEQ ID NO: 11, and
   an HVR-L3 comprising the amino acid sequence of SEQ ID NO, 12;
   and
   (b) a CD3 binding domain comprising the following six HVRs:
   an HVR-H1 comprising the amino acid sequence of SEQ ID NO:45,
   an HVR-H2 comprising the amino acid sequence of SEQ ID NO:46,
   an HVR-H3 comprising the amino acid sequence of SEQ ID NO:47,
   an HVR-L1 comprising the amino acid sequence of SEQ ID NO:48,
   an HVR-L2 comprising the amino acid sequence of SEQ ID NO:49, and
   an HVR-L3 comprising the amino acid sequence of SEQ ID NO:50.

6. The bispecific antibody of claim 5, wherein the CD3 binding domain comprises
   (a) a VH sequence having at least 95% sequence identity to the amino acid sequence of SEQ ID NO:59;
   (b) a VL sequence having at least 95% sequence identity to the amino acid sequence of SEQ ID NO:60; or
   (c) a VH sequence as in (a) and a VL sequence as in (b).

7. The bispecific antibody of claim 5, wherein the CD3 binding domain comprises a VH sequence of SEQ ID NO:59 and a VL sequence of SEQ ID NO:60.

8. A bispecific antibody that binds to CD79b and CD3, wherein the bispecific antibody comprises:
   (a) a CD79b binding domain comprising the following six hypervariable regions (HVRs):
   an HVR-H1 comprising the amino acid sequence of SEQ ID NO: 4,
   an HVR-H2 comprising the amino acid sequence of SEQ ID NO: 7,
   an HVR-H3 comprising the amino acid sequence of SEQ ID NO: 9,
   an HVR-L1 comprising the amino acid sequence of SEQ ID NO: 10,
   an HVR-L2 comprising the amino acid sequence of SEQ ID NO: 11, and
   an HVR-L3 comprising the amino acid sequence of SEQ ID NO, 12;
   and
   (b) a CD3 binding domain comprising the following six HVRs:

an HVR-H1 comprising the amino acid sequence of SEQ ID NO:45, an HVR-H2 comprising the amino acid sequence of SEQ ID NO:46, an HVR-H3 comprising the amino acid sequence of SEQ ID NO:47, an HVR-L1 comprising the amino acid sequence of SEQ ID NO:48, an HVR-L2 comprising the amino acid sequence of SEQ ID NO:49, and an HVR-L3 comprising the amino acid sequence of SEQ ID NO:50.

9. The bispecific antibody of claim 8, wherein the CD3 binding domain comprises
   (a) a VH sequence having at least 95% sequence identity to the amino acid sequence of SEQ ID NO:59;
   (b) a VL sequence having at least 95% sequence identity to the amino acid sequence of SEQ ID NO:60; or
   (c) a VH sequence as in (a) and a VL sequence as in (b).

10. The bispecific antibody of claim 8, wherein the CD3 binding domain comprises a VH sequence of SEQ ID NO:59 and a VL sequence of SEQ ID NO:60.

11. The bispecific antibody of claim 8, wherein the CD79b binding domain comprises
    (a) a VH sequence having at least 95% sequence identity to the amino acid sequence of SEQ ID NO: 19;
    (b) a VL sequence having at least 95% sequence identity to the amino acid sequence of SEQ ID NO:20; or
    (c) a VH sequence as in (a) and a VL sequence as in (b).

12. The bispecific antibody of claim 8, wherein the CD79b binding domain comprises a VH sequence of SEQ ID NO: 19 and a VL sequence of SEQ ID NO:20.

13. A bispecific antibody that binds to CD79b and CD3, wherein the bispecific antibody comprises:
    (a) a CD79b binding domain comprising a VH sequence of SEQ ID NO: 19 and a VL sequence of SEQ ID NO:20, and
    (b) a CD3 binding domain comprising a VH sequence of SEQ ID NO:59 and a VL sequence of SEQ ID NO:60.

14. The bispecific antibody of claim 8, wherein the bispecific antibody has a B cell killing EC50 of less than about 100 ng/mL.

15. The bispecific antibody of claim 14, wherein the B cell killing is endogenous B cell killing.

16. The bispecific antibody of claim 8, wherein the bispecific antibody has a cytotoxic T cell activation EC50 is less than about any of 50 ng/mL.

17. The bispecific antibody of claim 1, wherein (a) the CD3 binding domain comprises a Fc domain, wherein the Fc domain comprises T366S, L368A, Y407V, and N297G substitution mutations according EU numbering and (b) the CD79b binding domain comprises a Fc domain, wherein the Fc domain comprises T366W and N297G substitution mutations according EU numbering.

18. An isolated nucleic acid encoding the bispecific antibody of claim 1.

19. A vector comprising the isolated nucleic acid of claim 18.

20. A host cell comprising the vector of claim 19.

21. A method of producing a bispecific antibody, the method comprising culturing the host cell of claim 20 in a culture medium.

22. A pharmaceutical composition comprising the bispecific antibody of claim 1.

23. The bispecific antibody of claim 15, wherein the B cell killing is cell line B cell killing using a cell line selected from the group consisting of BJAB cell line, WSU-CLCL2 cell line, and OCI-Ly-19 cell line.

* * * * *

SEQUENCE LISTING

<160> NUMBER OF SEQ ID NOS: 64

<210> SEQ ID NO 1
<211> LENGTH: 179
<212> TYPE: PRT
<213> ORGANISM: Homo sapiens

<400> SEQUENCE: 1

Arg Phe Ile Ala Arg Lys Arg Gly Phe Thr Val Lys Met His Cys Tyr
1               5                   10                  15

Met Asn Ser Ala Ser Gly Asn Val Ser Trp Leu Trp Lys Gln Glu Met
            20                  25                  30

Asp Glu Asn Pro Gln Gln Leu Lys Leu Glu Lys Gly Arg Met Glu Glu
        35                  40                  45

Ser Gln Asn Glu Ser Leu Ala Thr Leu Thr Ile Gln Gly Ile Arg Phe
    50                  55                  60

Glu Asp Asn Gly Ile Tyr Phe Cys Gln Gln Lys Cys Asn Asn Thr Ser
65                  70                  75                  80

Glu Val Tyr Gln Gly Cys Gly Thr Glu Leu Arg Val Met Gly Phe Ser
                85                  90                  95

Thr Leu Ala Gln Leu Lys Gln Arg Asn Thr Leu Lys Asp Gly Ile Ile
            100                 105                 110

Met Ile Gln Thr Leu Leu Ile Ile Leu Phe Ile Ile Val Pro Ile Phe
        115                 120                 125

Leu Leu Leu Asp Lys Asp Asp Ser Lys Ala Gly Met Glu Glu Asp His
    130                 135                 140

Thr Tyr Glu Gly Leu Asp Ile Asp Gln Thr Ala Thr Tyr Glu Asp Ile
145                 150                 155                 160

Val Thr Leu Arg Thr Gly Glu Val Lys Trp Ser Val Gly Glu His Pro
                165                 170                 175

Gly Gln Glu

<210> SEQ ID NO 2
<211> LENGTH: 201
<212> TYPE: PRT
<213> ORGANISM: Homo sapiens

<400> SEQUENCE: 2

Ala Arg Ser Glu Asp Arg Tyr Arg Asn Pro Lys Gly Ser Ala Cys Ser
1               5                   10                  15

Arg Ile Trp Gln Ser Pro Arg Phe Ile Ala Arg Lys Arg Gly Phe Thr
            20                  25                  30

Val Lys Met His Cys Tyr Met Asn Ser Ala Ser Gly Asn Val Ser Trp

```
                35                  40                  45
Leu Trp Lys Gln Glu Met Asp Glu Asn Pro Gln Gln Leu Lys Leu Glu
 50                  55                  60

Lys Gly Arg Met Glu Glu Ser Gln Asn Glu Ser Leu Ala Thr Leu Thr
 65                  70                  75                  80

Ile Gln Gly Ile Arg Phe Glu Asp Asn Gly Ile Tyr Phe Cys Gln Gln
                 85                  90                  95

Lys Cys Asn Asn Thr Ser Glu Val Tyr Gln Gly Cys Gly Thr Glu Leu
            100                 105                 110

Arg Val Met Gly Phe Ser Thr Leu Ala Gln Leu Lys Gln Arg Asn Thr
        115                 120                 125

Leu Lys Asp Gly Ile Ile Met Ile Gln Thr Leu Leu Ile Ile Leu Phe
130                 135                 140

Ile Ile Val Pro Ile Phe Leu Leu Leu Asp Lys Asp Asp Ser Lys Ala
145                 150                 155                 160

Gly Met Glu Glu Asp His Thr Tyr Glu Gly Leu Asp Ile Asp Gln Thr
                165                 170                 175

Ala Thr Tyr Glu Asp Ile Val Thr Leu Arg Thr Gly Glu Val Lys Trp
            180                 185                 190

Ser Val Gly Glu His Pro Gly Gln Glu
        195                 200

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Tyr Trp Met Asn
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Tyr Tyr Met Asn
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Trp or Tyr

<400> SEQUENCE: 5

Thr Tyr Xaa Met Asn
1               5
```

```
<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Ile Asp Pro Ser Asp Ser Glu Thr His Tyr Asn Gln Met Phe Lys
1               5                   10                  15

Asp

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Ile Asp Pro Ser Asp Ser Glu Thr His Tyr Asn Gln Lys Phe Gln
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met or Lys
<220> FEATURE:
<221> NAME/KEY: MOD_RES
<222> LOCATION: (16)..(16)
<223> OTHER INFORMATION: Lys or Gln
<220> FEATURE:
<221> NAME/KEY: MOD_RES
<222> LOCATION: (17)..(17)
<223> OTHER INFORMATION: Asp or Gly

<400> SEQUENCE: 8

Met Ile Asp Pro Ser Asp Ser Glu Thr His Tyr Asn Gln Xaa Phe Xaa
1               5                   10                  15

Xaa

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Leu Ala Phe
1

<210> SEQ ID NO 10
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 10

Lys Ser Ser Gln Ser Leu Leu Asp Ser Asp Gly Lys Thr Tyr Leu Asn
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Val Ser Lys Leu Asp Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Gln Gly Thr His Phe Pro Gln Thr
1               5

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Ile
            35                  40                  45

Gly Trp Ile Asn Pro Gly Ser Gly Asn Thr Asn Tyr Ala Gln Lys Phe
        50                  55                  60

Gln Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Phe Asp Tyr Trp Gly Gln Gly Thr Leu Val Thr Val Ser Ser
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Met Thr Gln Thr Pro Leu Ser Leu Pro Val Thr Pro Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Ala
                85                  90                  95

Ile Gln Phe Pro Phe Thr Phe Gly Gln Gly Thr Lys Val Glu Ile Lys
            100                 105                 110

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Gln Pro Gly Val Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met Asn Trp Val Arg Gln Arg Pro Gly Gln Gly Leu Asp Trp Ile
        35                  40                  45

Gly Met Ile Asp Pro Ser Asp Ser Glu Thr His Tyr Asn Gln Met Phe
    50                  55                  60

Lys Asp Lys Ala Thr Leu Thr Val Asp Lys Ser Ser Ser Thr Ala Tyr
65                  70                  75                  80

Ile Gln Leu Asn Ser Leu Thr Ser Glu Asp Ser Ala Val Tyr Tyr Cys
                85                  90                  95

Ser Arg Ser Leu Ala Phe Trp Gly Gln Gly Thr Leu Val Thr Val Ser
            100                 105                 110

Ala

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Cys Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile

```
                65                  70                  75                  80
Ser Arg Val Glu Ala Glu Asp Leu Gly Val Tyr Tyr Cys Trp Gln Gly
                    85                  90                  95

Thr His Phe Pro Gln Thr Phe Gly Gly Gly Thr Lys Leu Glu Ile Lys
                    100                 105                 110

<210> SEQ ID NO 17
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Trp Met Asn Trp Val Arg Gln Ala Pro Gly Gln Gly Leu Glu Trp Ile
            35                  40                  45

Gly Met Ile Asp Pro Ser Asp Ser Glu Thr His Tyr Asn Gln Met Phe
    50                  55                  60

Lys Asp Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ser Arg Ser Leu Ala Phe Trp Gly Gln Gly Thr Leu Val Thr Val Ser
                100                 105                 110

Ser

<210> SEQ ID NO 18
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Lys Pro Gly Gln Ser
            35                  40                  45

Pro Gln Ser Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gln Gly Thr Lys Val Glu Ile Lys
                100                 105                 110

<210> SEQ ID NO 19
<211> LENGTH: 113
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Tyr Met Asn Trp Val Arg Gln Ala Pro Gly Gln Gly Leu Glu Trp Ile
            35                  40                  45

Gly Met Ile Asp Pro Ser Asp Ser Glu Thr His Tyr Asn Gln Lys Phe
50                  55                  60

Gln Gly Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ser Arg Ser Leu Ala Phe Trp Gly Gln Gly Thr Leu Val Thr Val Ser
                100                 105                 110

Ser

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Lys Pro Gly Gln Ser
            35                  40                  45

Pro Gln Ser Leu Ile Tyr Leu Val Ser Lys Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gln Gly Thr Lys Val Glu Ile Lys
                100                 105                 110

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Trp Met Asn Trp Val Arg Gln Ala Pro Gly Gln Gly Leu Glu Trp Ile
```

```
                35                  40                  45
Gly Met Ile Asp Pro Ser Asp Ser Glu Thr His Tyr Asn Gln Met Phe
            50                  55                  60

Lys Asp Arg Ala Thr Leu Thr Val Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ser Arg Ser Leu Ala Phe Trp Gly Gln Gly Thr Leu Val Thr Val Ser
            100                 105                 110

Ser
```

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Asp Val Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
            35                  40                  45

Pro Gln Ser Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gln Gly Thr Lys Val Glu Ile Lys
            100                 105                 110
```

<210> SEQ ID NO 23
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met Asn Trp Val Arg Gln Ala Pro Gly Gln Gly Leu Glu Trp Ile
            35                  40                  45

Gly Met Ile Asp Pro Ser Asp Ser Glu Thr His Tyr Asn Gln Met Phe
            50                  55                  60

Lys Asp Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ser Arg Ser Leu Ala Phe Trp Gly Gln Gly Thr Leu Val Thr Val Ser
            100                 105                 110
```

Ser

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Asp Ile Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Ser Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gln Gly Thr Lys Val Glu Ile Lys
            100                 105                 110
```

<210> SEQ ID NO 25
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met Asn Trp Val Arg Gln Ala Pro Gly Gln Gly Leu Glu Trp Ile
        35                  40                  45

Gly Met Ile Asp Pro Ser Asp Ser Glu Thr His Tyr Asn Gln Met Phe
    50                  55                  60

Lys Asp Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ser Arg Ser Leu Ala Phe Trp Gly Gln Gly Thr Leu Val Thr Val Ser
            100                 105                 110
```

Ser

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Val Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Ser Leu Ile Tyr Leu Val Ser Lys Leu Asp Ser Gly Val Pro
50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Trp Gln Gly
                85                  90                  95

Thr His Phe Pro Gln Thr Phe Gly Gln Gly Thr Lys Val Glu Ile Lys
                100                 105                 110

<210> SEQ ID NO 27
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met Asn Trp Val Arg Gln Ala Pro Gly Gln Gly Leu Glu Trp Ile
        35                  40                  45

Gly Met Ile Asp Pro Ser Asp Ser Glu Thr His Tyr Asn Gln Met Phe
50                  55                  60

Lys Asp Arg Ala Thr Ile Thr Val Asp Thr Ser Thr Ser Thr Ala Tyr
65              70                  75                  80

Leu Glu Leu Ser Ser Leu Arg Ser Glu Asp Thr Ala Val Tyr Tyr Cys
                85                  90                  95

Ser Arg Ser Leu Ala Phe Trp Gly Gln Gly Thr Leu Val Thr Val Ser
                100                 105                 110

Ser

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Val Met Thr Gln Thr Pro Leu Ser Leu Pro Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Ser Leu Ile Tyr Leu Val Ser Lys Leu Asp Ser Gly Val Pro
50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Gln Thr Phe Gly Gln Gly Thr Lys Val Glu Ile Lys
             100                 105                 110
```

<210> SEQ ID NO 29
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                 20                  25                  30

Trp Met Asn Trp Val Arg Gln Ala Pro Gly Gln Gly Leu Glu Trp Ile
             35                  40                  45

Gly Met Ile Asp Pro Ser Asp Ser Glu Thr His Tyr Asn Gln Met Phe
 50                  55                  60

Lys Asp Arg Val Thr Leu Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ser Arg Ser Leu Ala Phe Trp Gly Gln Gly Thr Leu Val Thr Val Ser
             100                 105                 110

Ser
```

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Asp Ile Val Met Thr Gln Thr Pro Leu Ser Leu Pro Val Thr Pro Gly
 1               5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Leu Leu Gln Lys Pro Gly Gln Ser
             35                  40                  45

Pro Gln Ser Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Gln Thr Phe Gly Gln Gly Thr Lys Val Glu Ile Lys
             100                 105                 110
```

<210> SEQ ID NO 31
<211> LENGTH: 5
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 31

Ser Tyr Trp Ile Glu
1               5

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Glu Ile Leu Pro Gly Gly Gly Asp Thr Asn Tyr Asn Glu Ile Phe Lys
1               5                   10                  15

Gly

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Val Pro Ile Arg Leu Asp Tyr
1               5

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Ala Ser Gln Ser Val Asp Tyr Asp Gly Asp Ser Phe Leu Asn
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ala Arg Lys Leu Gly Arg
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

Gln Gln Ser Asn Glu Asp Pro Leu Thr
1               5

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Val
        35                  40                  45

Gly Glu Ile Leu Pro Gly Gly Gly Asp Thr Asn Tyr Asn Glu Ile Phe
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
        115

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Arg Lys Leu Gly Arg Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys
            100                 105                 110

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 39

Asn Tyr Tyr Ile His
1               5

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Ile Tyr Pro Gly Asp Gly Asn Thr Lys Tyr Asn Glu Lys Phe Lys
1               5                   10                  15
Gly

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Ser Tyr Ser Asn Tyr Tyr Phe Asp Tyr
1               5                   10

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Ser Ser Gln Ser Leu Leu Asn Ser Arg Thr Arg Lys Asn Tyr Leu
1               5                   10                  15
Ala

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Ala Ser Thr Arg Glu Ser
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Gln Ser Phe Ile Leu Arg Thr
1               5
```

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Tyr Tyr Ile His
1               5

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Ile Tyr Pro Glu Asn Asp Asn Thr Lys Tyr Asn Glu Lys Phe Lys
1               5                   10                  15

Asp

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Gly Tyr Ser Arg Tyr Tyr Phe Asp Tyr
1               5                   10

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Ser Ser Gln Ser Leu Leu Asn Ser Arg Thr Arg Lys Asn Tyr Leu
1               5                   10                  15

Ala

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Trp Thr Ser Thr Arg Lys Ser
1               5

<210> SEQ ID NO 50
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 50

Lys Gln Ser Phe Ile Leu Arg Thr
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Tyr Thr Met Asn
1               5

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Ile Asn Pro Tyr Lys Gly Val Ser Thr Tyr Asn Gln Lys Phe Lys
1               5                   10                  15

Asp

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Gly Tyr Tyr Gly Asp Ser Asp Trp Tyr Phe Asp Val
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ala Ser Gln Asp Ile Arg Asn Tyr Leu Asn
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Tyr Thr Ser Arg Leu Glu Ser
```

```
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Gly Asn Thr Leu Pro Trp Thr
1               5

<210> SEQ ID NO 57
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95
```

```
Ser Phe Ile Leu Arg Thr Phe Gly Gln Gly Thr Lys Val Glu Ile Lys
                100                 105                 110
```

<210> SEQ ID NO 59
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
                20                  25                  30

Tyr Ile His Trp Val Arg Gln Ala Pro Gly Gln Gly Leu Glu Trp Ile
                35                  40                  45

Gly Trp Ile Tyr Pro Glu Asn Asp Asn Thr Lys Tyr Asn Glu Lys Phe
        50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
                100                 105                 110

Thr Leu Val Thr Val Ser Ser
        115
```

<210> SEQ ID NO 60
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
                35                  40                  45

Ser Pro Lys Leu Leu Ile Tyr Trp Thr Ser Arg Lys Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
                100                 105                 110
```

<210> SEQ ID NO 61
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Asp Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Leu Lys
            100                 105

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Arg Ser Glu Asp Arg Tyr Arg Asn Pro Lys Gly Ser Ala Cys Ser
1               5                   10                  15

Arg Ile Trp Gln Ser
            20

<210> SEQ ID NO 64
<211> LENGTH: 21

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Lys Ser Glu Asp Leu Tyr Pro Asn Pro Lys Gly Ser Ala Cys Ser
1               5                   10                  15

Arg Ile Trp Gln Ser
            20
```